United States Patent
Kline et al.

(10) Patent No.: US 9,068,912 B2
(45) Date of Patent: Jun. 30, 2015

(54) WEARABLE ARTICLE WITH EXTENSIBLE FASTENING MEMBER HAVING STRESS DISTRIBUTION FEATURES AND/OR FASTENING COMBINATION PERFORMANCE CHARACTERISTICS

(75) Inventors: Mark James Kline, Okeana, OH (US); Oliver Edwin Clarke Mason, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 337 days.

(21) Appl. No.: 12/904,220

(22) Filed: Oct. 14, 2010

(65) Prior Publication Data
US 2011/0092947 A1 Apr. 21, 2011

Related U.S. Application Data
(60) Provisional application No. 61/251,875, filed on Oct. 15, 2009.

(51) Int. Cl.
| | |
|---|---|
| *A61F 13/15* | (2006.01) |
| *G01N 3/08* | (2006.01) |
| *G01N 19/04* | (2006.01) |
| *A61F 13/49* | (2006.01) |
| *A61F 13/62* | (2006.01) |

(52) U.S. Cl.
CPC .......... *G01N 19/04* (2013.01); *A61F 13/49015* (2013.01); *A61F 13/62* (2013.01); *G01N 2203/0016* (2013.01); *G01N 2203/0025* (2013.01); *G01N 2203/0091* (2013.01)

(58) Field of Classification Search
USPC ................... 73/760, 761, 831, 826, 834, 835; 24/306, 442; 604/391
See application file for complete search history.

(56) References Cited

U.S. PATENT DOCUMENTS

| | | | |
|---|---|---|---|
| 3,882,871 A * | 5/1975 | Taniguchi | ..................... 604/372 |
| 4,107,364 A | 8/1978 | Sisson | |
| 4,834,741 A | 5/1989 | Sabee | |
| 4,846,815 A | 7/1989 | Scripps | |
| 5,156,793 A | 10/1992 | Buell et al. | |
| 5,167,897 A | 12/1992 | Weber et al. | |
| 5,984,911 A * | 11/1999 | Siebers et al. | ................ 604/391 |

(Continued)

FOREIGN PATENT DOCUMENTS

| | | |
|---|---|---|
| EP | 1 655 006 B1 | 8/2007 |
| GB | 2 201 796 A | 9/1988 |
| WO | WO-92/15446 A1 | 9/1992 |

OTHER PUBLICATIONS

International Search Report, dated Feb. 24, 2011—5 pages.

*Primary Examiner* — Harshad R Patel
(74) *Attorney, Agent, or Firm* — William E. Gallagher

(57) ABSTRACT

A wearable article with an extensible fastening member having a fastener proximate its end is disclosed. The fastening member may be highly extensible, and may have construction features and shape characteristics that affect distribution of force components when the fastener is in use, and reduce the chances of buckling or flipping of the fastening member along its edges, and the chances that the edges of the fastener will be lifted away from a surface to which it is attached. The fastener and material forming an accompanying landing zone on the article may be selected to form a fastening combination having performance attributes that provide further resistance to unintended pop-off under wearing conditions.

15 Claims, 21 Drawing Sheets

(56) References Cited

U.S. PATENT DOCUMENTS

| | | |
|---|---|---|
| 6,506,186 B1 | 1/2003 | Roessler et al. |
| 7,105,107 B2 | 9/2006 | Ramani et al. |
| 7,195,729 B2 | 3/2007 | Jackson et al. |
| 7,217,262 B2 * | 5/2007 | Nakahata et al. .............. 604/391 |
| 7,414,269 B2 | 8/2008 | Grötsch et al. |
| 7,799,162 B2 | 9/2010 | Wood et al. |
| 8,790,326 B2 * | 7/2014 | Kline et al. .................... 604/386 |
| 8,808,267 B2 * | 8/2014 | Kline et al. .................... 604/386 |
| 8,845,610 B2 * | 9/2014 | Kline et al. .................... 604/386 |
| 2003/0054740 A1 | 3/2003 | Mansky |
| 2003/0088220 A1 | 5/2003 | Molander et al. |
| 2004/0181200 A1 | 9/2004 | Desai et al. |
| 2004/0193133 A1 | 9/2004 | Desai et al. |
| 2006/0293639 A1 | 12/2006 | Van Gompel et al. |
| 2007/0142815 A1 | 6/2007 | Macura et al. |
| 2007/0143972 A1 | 6/2007 | Kline et al. |
| 2007/0156111 A1 | 7/2007 | Dalal et al. |
| 2007/0157441 A1 | 7/2007 | Kline et al. |
| 2007/0287982 A1 | 12/2007 | Lodge et al. |
| 2007/0293111 A1 | 12/2007 | Mansfield |
| 2008/0021432 A1 * | 1/2008 | Kline et al. ................... 604/391 |
| 2008/0167635 A1 | 7/2008 | Kline et al. |
| 2010/0280481 A1 | 11/2010 | Kline et al. |
| 2010/0280482 A1 | 11/2010 | Kline et al. |
| 2010/0280483 A1 | 11/2010 | Kline et al. |
| 2010/0280484 A1 | 11/2010 | Kline et al. |

* cited by examiner

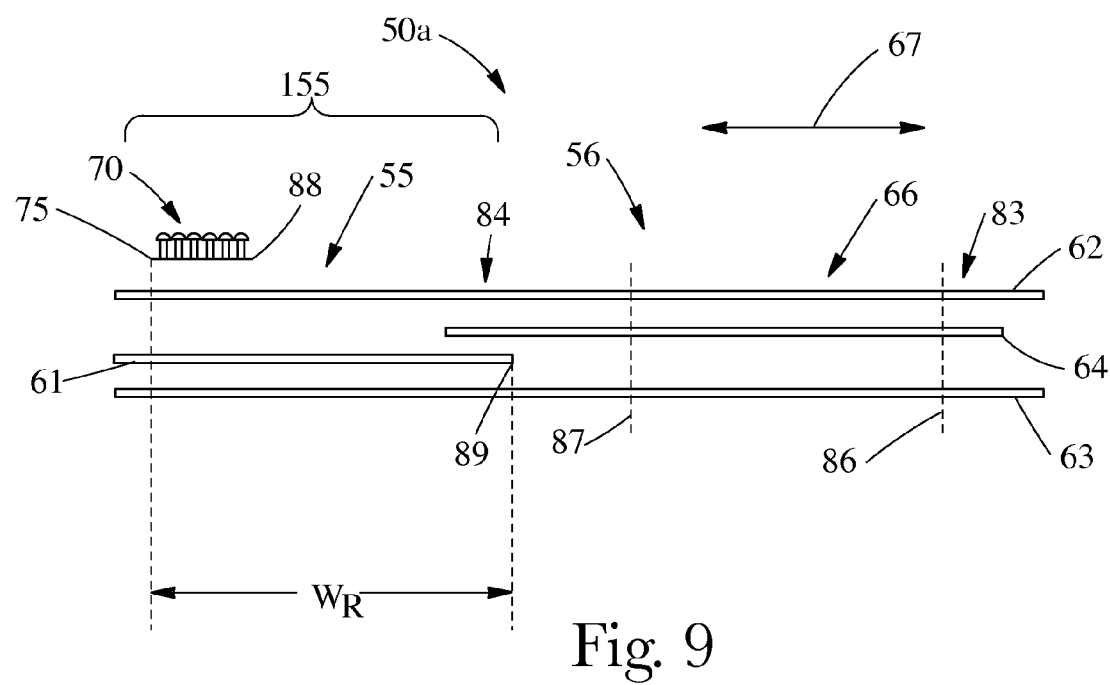

WEARABLE ARTICLE WITH EXTENSIBLE FASTENING MEMBER HAVING STRESS DISTRIBUTION FEATURES AND/OR FASTENING COMBINATION PERFORMANCE CHARACTERISTICS

CROSS-REFERENCE TO RELATED APPLICATIONS

This application claims the benefit of U.S. Provisional Application No. 61/251,875, filed Oct. 15, 2009, the substance of which is incorporated herein by reference.

BACKGROUND OF THE INVENTION

Some wearable articles are manufactured to include fastening members. For example, some varieties of diapers are manufactured with a pair of oppositely-oriented side fastening members, extending laterally from each side of a first waist region of the chassis, each fastening member having a fastener located at or near the outboard end thereof, and adapted to attach or adhere to a fastener receiving zone ("landing zone") disposed on a second waist region of the chassis. The fastening members may be formed in part or in whole of a nonwoven web material. In some examples, the fastening members are formed at least in part of a laminate of one or more layers of nonwoven web material and one or more layers or strands of a polymeric elastic material, and fashioned and adapted in such a way as to be elastically extensible in at least the direction in which the fastening member is to be pulled during application and use. One type has fastening members extending from the rear waist region of the diaper, and is intended to enable the person applying the diaper (hereinafter, "applier") to lay the diaper open on a surface, with the rear region of the diaper beneath a reclining wearer's bottom, wrap the chassis forward between the wearer's legs and up over the front of the lower torso, draw each fastening member from the rear waist region around a hip, and attach the end of each fastening member to the front region via the fastener, thereby forming a waistband and pant-like structure about the wearer. When the diaper is applied, each fastening member may be in direct contact with the wearer's skin at a hip.

In some examples of diapers having fastening members, it may be desirable that the fastening members be formed so as to cover substantial areas of skin at the wearer's hips. This may have two purposes, among others: First, comfort, resulting from distribution of normal force components of tension forces in the fastening members over greater, rather than lesser, areas of skin; and second, appearance.

It also may be desirable to form fastening members from material that is relatively soft to the touch, pliable and stretchy. Purposes for this may include comfort.

Fastening members may be subject to varying forces, resulting from tugging during application, and from the wearer's movements at the hips, particularly if the diaper is snugly applied. These forces may have various undesirable effects. A typical fastening member, e.g., one that extends from the rear waist region of a diaper, is longer at its inboard end than at its outboard end. This general geometry may be incorporated to allow for, e.g., better fit about the wearer's hips, and better distribution of lateral tension forces along a greater length along the location(s) where the fastening member joins the rear waist region, thereby reducing the likelihood of tearing along that line or locations proximate the inboard end of the fastening member. Conversely, a relatively shorter outboard end, typically having a fastener attached proximate thereto, allows for tugging by the applier by simply grasping between thumb and forefinger, and for easy selection and placement of a point or region of fastening, by simply placing the grasped, shortened outboard end at the desired location. This general geometry results in lateral tension forces being focused from a longer inboard region to a shorter outboard end region of the fastening member. This focusing, together with stretching, creates longitudinal force components within the fastening member.

Longitudinal force components acting within the fastening member may create the likelihood that portions of the fastening member such as a panel region and/or extensible zone thereof will undesirably laterally buckle and/or flip away from the wearer. For purposes of maximizing skin coverage for best appearance, evenly distributing forces, and wearer comfort, panel regions of fastening members may be formed so as to have the greatest length (in a longitudinal direction along the chassis) feasible under the circumstances. Increasing length adds to the area of the material forming the panel region. With increasing length and surface area of the panel region, undesirable buckling/flipping of the panel region material proximate either the top or bottom edges may be more likely, particularly when the wearer bends at the hips. This problem may be more likely to manifest itself in "tape" type fastening members, in which a comparatively short tab member, bearing a fastener and forming the end region of the fastening member, joins a relatively longer side panel region, such that a step-wise decrease in length of the fastening member exists where the panel region ends and the tab member extends therefrom. When the panel region and/or an extensible zone thereof is highly extensible (and relatively pliable), it may tend to buckle and flip about the relatively short tab member.

In examples in which a layer forming an end region of a fastening member is coextensive in length, or longer than, a layer of material forming the region immediately inboard of the end region, buckling/flipping of the panel region proximate its edges may be less likely because longitudinal force components resulting from lateral tension in the fastening member may be distributed into the end region. As a result, however, such longitudinal force components may act at or about the lateral edges of the fastener and contribute to causing the fastener to bend or "dish", i.e., contribute to causing its lateral edges to be urged to turn up and away from the surface to which it is attached. For example, one type of diaper fastening member may include a fastener consisting of a patch of hooks, a component of a hook-and-loop fastening system (such as a 3M, APLIX or VELCRO hook-and-loop system). A patch of a corresponding loops component may be disposed at a landing zone on the outside front waist region of the diaper, so as to enable attachment when the hooks patch is pressed against the landing zone. Another example may have a fastener consisting of a patch of material bearing an adhesive effective to adhere to a smooth surface disposed at the landing zone. Upon being tugged laterally by an applier during application, and/or with lateral tension resulting from application and/or the wearer's movements, longitudinal force components of tension forces in the fastening member, acting at the edges of the fastener patch, can urge its longitudinally outer edges up and away from the landing zone, thereby causing a sub-optimal fastener attachment to the landing zone, or weakening the fastener's hold at the landing zone, or even causing the fastener's hold to fail—which may allow the diaper to come loose or fall free of the wearer.

In some circumstances, stresses in the fastening member resulting from lateral tension may concentrate in the end region near or at the inboard edges of the fastener zone. As a result, the likelihood of a tear beginning at the location of stress concentration is increased. For example, stresses may be concentrated at locations where the fastening member narrows to an end region, particularly if there is an abrupt structural discontinuity, such as created by the presence of, for example, the edge of a patch of a relatively stiffer material adhered to a substrate material. Tearing may occur in the end region, at or near the fastener zone, when the applier tugs on the fastening member to apply the diaper; or the end region may tear at or near the fastener zone from stresses resulting from the wearer's movements.

The above-described events, i.e., panel region buckling/flipping, fastener dishing, and tearing, may be deemed problematic because they may result in less than optimum performance and/or appearance, failure of the product, and consumer dissatisfaction.

Likelihood of the problems identified above may be decreased by the use of relatively more robust materials to form the fastening member. A material that is more robust, and therefore, stiffer and more resistive to buckling and tearing, may be used to form the panel region and/or extensible zone. Robustness of a material such as a stretch laminate can be increased, for example, by the use of materials having greater basis weights and/or densities. Similarly, increasing the bending stiffness of a fastener patch by selection of a thicker and/or denser patch material may make it more resistive to dishing.

These approaches, however, also may have undesirable consequences. If a fastener patch is too stiff and unyielding, when fastened at the wearer's waist it may feel like an unyielding object and be a source of discomfort for the wearer under certain circumstances. Increasing the strength of a stretch laminate may increase its stiffness, but decrease its extensibility and pliability, as well. Increasing the stiffness of a material that is against the wearer's skin in a region of the body subject to movement and bending may increase likelihood of discomfort for the wearer, and promote marking, irritation and chafing of the wearer's skin. For the manufacturer of disposable diapers, acceptable but relatively more robust materials may be relatively more expensive. If fastening members are not extensible, or not sufficiently so, then it may be necessary to build additional stretch features into, e.g., the waist regions of the chassis, if assurance of a comfortable and snug-fitting diaper is to be maintained.

From the foregoing it can be appreciated that the design of a fastening member involves a variety of concerns, and that a great number of variables and permutations in the combinations of materials, features and structures used is possible. Changing one material, feature or structure to address one concern may give rise to other concerns. A need for improvements in the combination of materials, features and structures used, that satisfactorily address and reduce concerns for comfort, performance and manufacturing cost of the fastening member and its associated wearable article, always exists.

BRIEF DESCRIPTION OF THE DRAWINGS

In the drawings, like numerals or other designations designate like features throughout the views.

FIG. 9 is a depiction of a simplified schematic, exploded lateral cross section through an example of a fastening member, taken along a stretch direction;

DETAILED DESCRIPTION OF THE INVENTION

For purposes of this Description, it is intended that the following terms have the meanings set forth:

As used herein, the term "extensible" refers to the property of a material, wherein: when a biasing force is applied to the material, the material can be extended to an elongated length of at least 110% of its original relaxed length (i.e. can extend 10%), without a rupture or breakage that renders the material unusable for its intended purpose. A material that does not meet this definition is considered inextensible. In some embodiments, an extensible material may be able to be extended to an elongated length of 125% or more of its original relaxed length without rupture or breakage that renders the material unusable for its intended purpose. An extensible material may or may not exhibit recovery after application of a biasing force.

Throughout the present description, an extensible material is considered to be "elastically extensible" if, when a biasing force is applied to the material, the material can be extended to an elongated length of at least 110% of its original relaxed length (i.e. can extend 10%), without rupture or breakage which renders the material unusable for its intended purpose, and when the force is removed from the material, the material recovers at least 40% of its elongation. In various examples, when the force is removed from an elastically extensible material, the material may recover at least 60% or at least 80% of its elongation.

"Inboard", and forms thereof, with respect to features of a fastening member, means furthest from or in a direction away from the free distal end.

Figure 2:
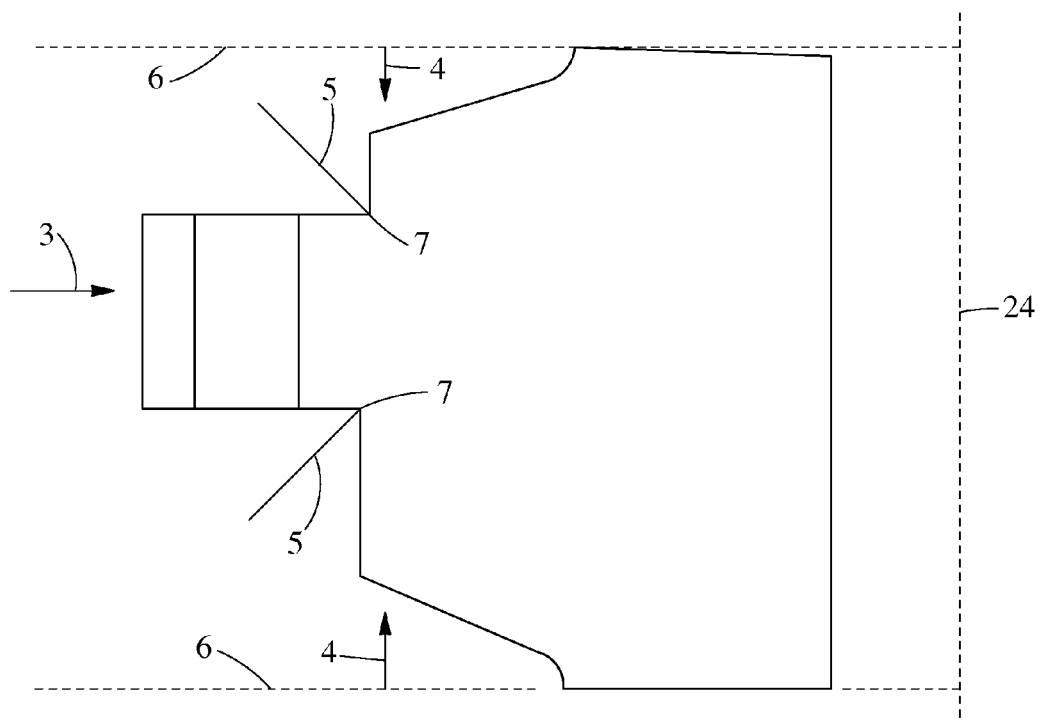
FIG. 2 is a depiction of an example of a fastening member, laid flat and viewed from above.

An "inboard- and longitudinally inward-pointing vertex", with respect to a feature of a lateral edge of a wearable article fastening member, laid flat and horizontally, viewed from above, is one in which a line equally dividing the angle formed by the vertex, together with the portions of the lines forming the vertex, form an arrow that points at least partially longitudinally inwardly on the fastening member and away from a lateral line perpendicular to the wearable article longitudinal axis and intersecting the longitudinally outermost point along the lateral edge, and at least partially in a laterally inboard direction. Referring to FIG. 2, such inboard direction is indicated by arrow 3 (perpendicular to longitudinal axis 24); longitudinally inward directions are indicated by arrows 4 (parallel to longitudinal axis 24, and pointing away from lateral lines 6); and examples of inboard and longitudinally inward directions are indicated by arrows 5, formed at depicted examples of identifiable inboard- and longitudinally inward-pointing vertices 7.

"Junction line," with respect to a fastening member comprising components that are discrete from other components of a wearable article, which fastening member is welded, bonded, adhered or otherwise attached to the wearable article, means a longitudinal line, parallel with a longitudinal axis of the wearable article, across the fastening member through the inboard-most point at which the fastening member or a portion thereof is extensible in response to a lateral tension force imposed thereon. Note: In some examples of fastening members, an extensible zone might have an irregular shape or orientation, or consist of a plurality of extensible portions; in such examples, the point at which such shape, orientation or extensible portions are closest to a longitudinal axis of a wearable article will mark the location of the junction line. "Junction line," with respect to a fastening member comprising one or more components that are not discrete from, but rather, integral with, one or more components of a diaper chassis that is disposed in an opened, extended position and laid flat and horizontally, viewed from above, means either— (a) a longitudinal line along the fastening member and integral chassis component, parallel to the wearable article longitudinal axis, and aligned with the longitudinal edge of the chassis at its narrowest point, on the side from which the fastening member extends, or (b) a longitudinal line across the fastening member through the inboard-most point at which the fastening member or a portion thereof is extensible—whichever longitudinal line is most outboard along the fastening member, subject to the Note immediately above.

"Lateral" (and forms thereof), with respect to a line lying in a plane substantially occupied by a wearable article fastening member laid flat and horizontally, viewed from above, related to a direction substantially perpendicular to a longitudinal axis of the wearable article. "Lateral" and "width" (and forms thereof), with respect to features of a wearable article fastening member, relates to a direction, or generally following a direction, partially or entirely perpendicular to a longitudinal axis along the wearable article. "Lateral" and "width" (and forms thereof), with respect to features of a diaper chassis, relates to a direction substantially parallel to the lateral axis of the chassis.

"Lateral axis" with respect to a wearable article adapted to be worn by a wearer, means an axis perpendicular to the longitudinal axis, and equally dividing the longitudinal length of the article.

Where features or elements of claims set forth herein are identified as "lines" or "line segments" or "points", such lines, line segments or points are not actual physical features themselves unless otherwise specified, but rather, are geometric references intended for use in describing locations on a physical structure.

"Longitudinal" and "length" (and forms thereof), with respect to a line lying in a plane substantially occupied by a wearable article fastening member laid flat and horizontally, viewed from above, relates to a direction approximately aligned with the wearer's spine when the article would be normally worn, with the wearer in a standing or extended reclining position. "Longitudinal" and "length" (and forms thereof), with respect to features of a fastening member, relates to a direction, or generally following a direction approximately aligned with the wearer's spine when the article would be normally worn, with the wearer in a standing or extended reclining position. "Longitudinal" and "length" (and forms thereof), with respect to features of a diaper chassis, relates to a direction approximately aligned with the wearer's spine when the article would be normally worn, with the wearer in a standing or extended reclining position.

"Longitudinal axis" with respect to a wearable article adapted to be worn by a wearer, means an axis approximately aligned with the wearer's spine when the article would be normally worn, with the wearer in a standing or extended reclining position, and equally dividing the lateral width of the article, the lateral width being measured along a direction generally, parallel to the lateral axis.

Figure 1:
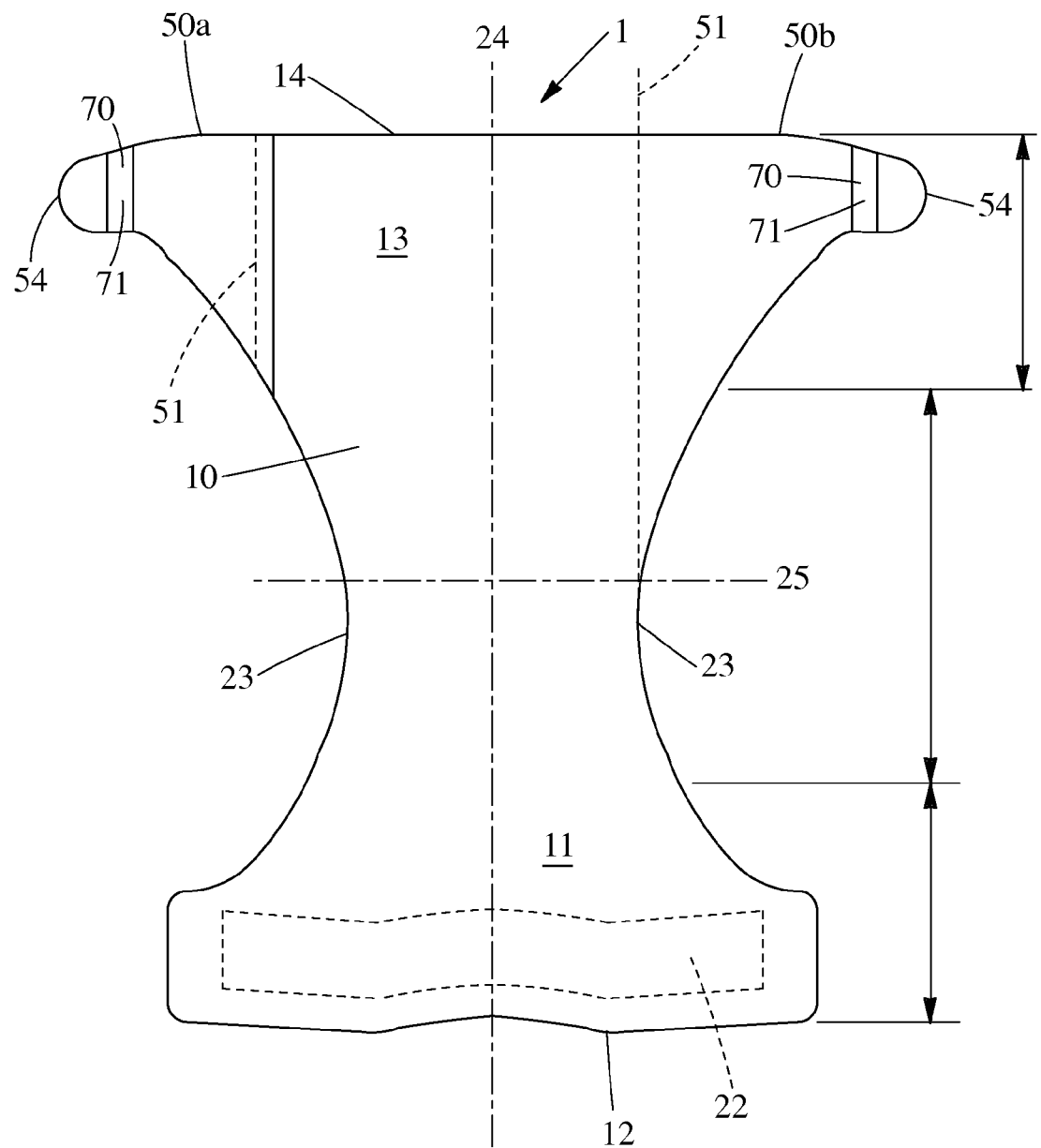
FIG. 1 is a simplified depiction of a wearable article in the form of a diaper, shown extended and laid flat, viewed from above, wearer-facing surface up.

"Longitudinal axis" with respect to a diaper chassis having a pair of opposing lateral waist edges and a pair of opposing longitudinal edges, the diaper chassis being opened and laid flat and horizontally, viewed from above, means a line connecting the waist edges and equidistant from the longitudinal edges, thus equally dividing the lateral width of the chassis, as illustrated by way of example in FIG. 1 (at reference numeral 24).

"Longitudinally inner", and forms thereof, with respect to a fastening member laid flat and horizontally, viewed from above, means at or toward its longitudinal middle, between its lateral edges.

"Longitudinally outer", and forms thereof, with respect to a fastening member laid flat and horizontally, viewed from above, means at or toward one of its lateral edges, and away from its longitudinal middle.

"Nonwoven" or "nonwoven material" means a fabric-like web material formed of fibers of a material (such as a polymeric material) which are neither woven nor knitted.

"Normal", when used in conjunction with the terms "direction", "force" and/or "stress" in a web material, refers to a direction approximately orthogonal to the macroscopic surface of the web material when laid flat, or approximately orthogonal to a plane that is tangential to the macroscopic planar surface of the web material when the macroscopic surface of the web material is curved.

"Outboard", and forms thereof, with respect to features of a fastening member, means at or in a direction toward its free distal end.

"Overlap" (and forms thereof), when used to describe a disposition of two or more discrete layers forming a fastening member, means that one layer lies, at least partially, vertically over or beneath the other(s) when the member is laid flat in horizontal position, as viewed from above. Unless otherwise specified, "overlap" is not intended to imply or be limited to meaning that the layers are in direct contact with each other, without any intermediate layers or other materials or structures between them.

"Stiffness", when capitalized, refers to a property of a portion of a fastening member as identified and determined by application of the Stiffness Test set forth herein.

"Stretch laminate" means an extensible and elastic web material comprising a combination of an elastic polymeric material layered, laminated or interspersed with a nonwoven material.

FIG. 1 generally depicts a simplified representation an example of a wearable article, in the form of a diaper 1, as it might appear in an opened, extended position, laid flat and horizontally, body-facing surface up, and viewed from above. Diaper 1 may have a chassis 10, longitudinal edges 23, longitudinal axis 24, lateral axis 25, front waist region 11, front waist edge 12, rear waist region 13, and rear waist edge 14, and an absorbent core (not shown) disposed between layers of the chassis 10. Chassis 10 may have a pair of oppositely-oriented fastening members 50a, 50b extending laterally from a waist region 11 or 13. A fastening member 50a may be a discrete component affixed to a portion of chassis 10 along a line as suggested on the left side of FIG. 1. In another example, however, a fastening member 50b may be a component that is not discrete from the chassis 10, but rather, may be integral with a chassis component such as a backsheet, forming an extension thereof, such as suggested on the right side of FIG. 1.

Each of fastening members 50a, 50b may have a respective fastener zone 71 that includes a fastener 70 disposed at or near its outboard end. In one example, a fastener 70 may be a patch of hook material constituting the hook components of a hook-and-loop fastening system (such as a 3M, APLIX or VEL-CRO hook-and-loop system). In this example, the garment-facing surface of front waist region 11 may have a laterally extended landing zone 22 bearing a patch or strip of loop material constituting the cooperating loop component of the hook-and-loop fastening system. In another example, a fastener 70 may be a patch of adhesive-bearing material, and landing zone 22 may bear a patch of adhesive-receiving material having smooth surface features and/or chemistry effective to provide an adhesive bond upon contact with a fastener 70. Other examples of fasteners include but are not limited to fastening elements described in co-pending U.S. application Ser. No. 11/895,169. Other examples may include any other cooperating engaging and receiving surfaces or components adapted to effect fastening, respective components of which may be disposed on either fastening zone 71 or landing zone 22, or another location of the wearable article as desired. A fastener 70 also may include groups of separately identifiable fastening elements such as a plurality of discrete patches of adhesive-bearing material, discrete patches of hooks, etc. In any of the above examples as well as other possible examples, the lateral extent of a landing zone 22 across front waist region 11 as suggested in FIG. 1 provides for attachment of fasteners 70 at laterally varying locations along the front waist region 11, and thereby, adjustability of the waist opening size and snugness of the diaper as it is being applied to a wearer.

Figure 3:
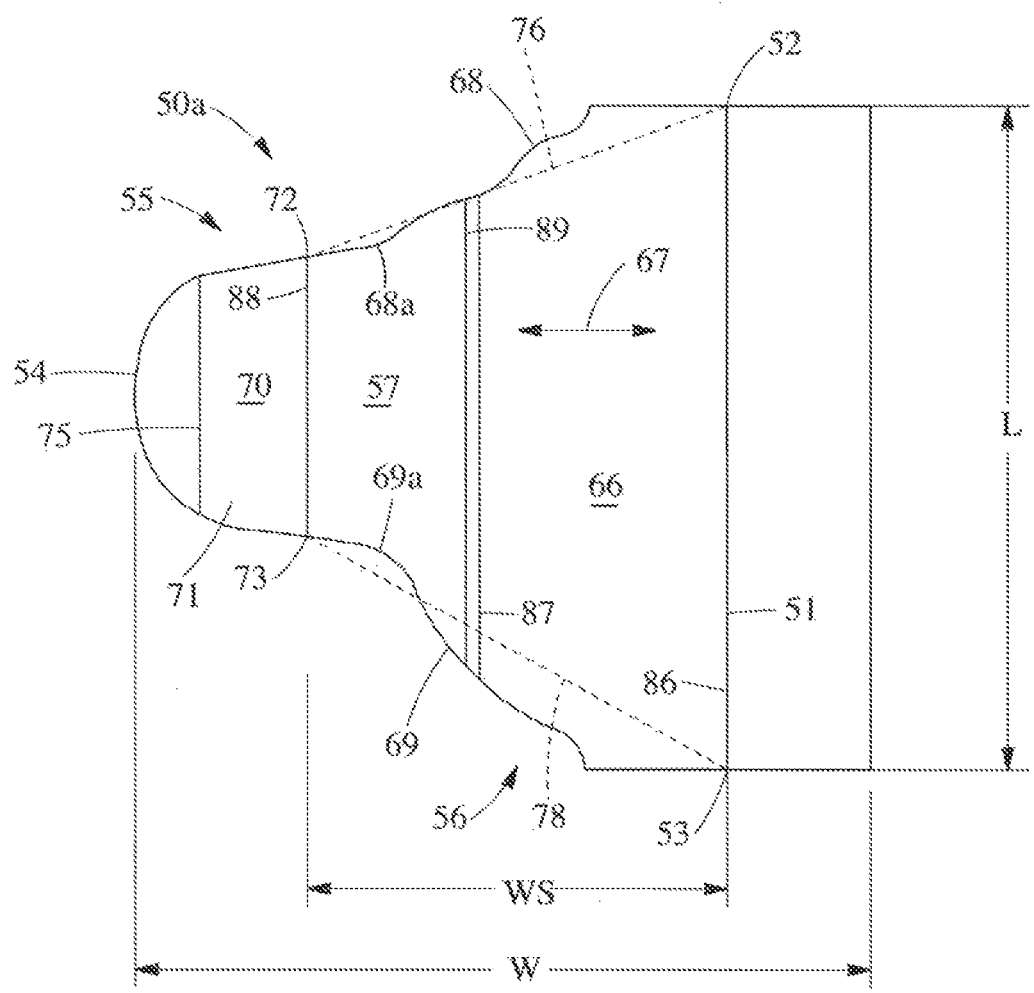
FIG. 3 is a depiction of an example of a fastening member, laid flat and viewed from above.

FIG. 3 depicts an example of a fastening member 50a shown apart from a wearable article. The fastening member 50a has a first longitudinally outermost lateral edge 68, a second longitudinally outermost lateral edge 69, and an outboard end 54. In examples such as those in which the wearable article is a diaper, in order to comfortably accommodate the wearer's movements while promoting a snug fit (and thus, optimal appearance and avoidance of leakage of the wearer's exudates), it may be desirable to form fastening member 50a with an extensible zone 66, which may comprise a laminate that is extensible along a stretch direction 67. In all examples discussed herein, extensible zone 66 may comprise a web or laminate web that is elastically extensible. Extensible zone 66 may extend between inboard and outboard extensible zone extents 86, 87. Outboard extensible zone extent 87 is a line drawn longitudinally through the outboard-most extent of the location(s) of extensible zone 66. (In some examples of fastening members, an extensible zone might have an irregular shape or orientation, or consist of a plurality of extensible portions; in such examples, the point at which such shape, orientation or extensible portions are farthest from a longitudinal axis of a wearable article will mark the location of the outboard extensible zone extent 87.) In examples having mechanical activation as described below, forming extensible zone 66, extensible zone extents 86, 87 may fall along inboard and outboard lines at which a region of mechanical activation is bounded. For all purposes herein, inboard extensible zone extent 86 is coincident with junction line 51. Fastening member 50a may be attached to a wearable article in any suitable manner, including, but not limited to, continuous or intermittent adhesive bonding, compression bonding, heat bonding, ultrasonic bonding, etc. Fastening zone 71 is bounded by fastening zone inboard extent 88 and fastening zone outboard extent 75; extents 88 and 75 are longitudinal lines, parallel with the longitudinal axis of the wearable article, along the inboard-most and outboard-most locations at which a fastener is located. Inboard fastener zone corners 72 and 73 are respective points on lateral edges 68, 69 intersected by fastener zone inboard extent 88. Note: In some examples of fastening members, a fastener might have an irregular shape or orientation, or consist of a plurality of discrete fastening elements; in such examples, the points at which such shape, orientation or elements are closest to and farthest from a longitudinal axis of a wearable article will mark the locations of the fastening zone inboard and outboard extents 88 and 75, respectively.

A junction line 51 on the fastening member can be identified as defined above, and intersects first and second outermost lateral edges 68, 69 at first and second longitudinally outermost junction points 52, 53. First and second line segments 76, 78, connecting first and second junction points 52, 53 and first and second inboard fastener zone corners 72, 73, respectively, can be identified. An end region 55 may project in an outboard direction from outboard extensible zone extent 87, and include an intermediate region 57. End region 55 may have a fastener 70 disposed at or near the outboard end 54 thereof. One or more layers of material forming end region 55 may be partially or entirely integral and continuous with layer(s) of material forming panel region 56, or end region 55 may be formed of differing or supplemental materials attached to panel region 56.

As noted in the Background, fastening members of a diaper may be designed and situated to wrap around a wearer's hips. As a result, they may be in Contact with the skin at the wearer's hips while the diaper is being worn. Additionally, while a diaper is being worn the fastening members will sustain and transfer varying tension forces, particularly when the wearer is active and bending at the hips. These tension forces have normal force components acting on the wearer's skin. Thus, it may be desirable that the material forming the skin-contacting portions of a fastening member 50a be selected with the objectives of maximizing extensibility, pliability and surface area. Increasing these variables generally may help to more evenly distribute normal forces over a greater skin surface area, provide for easier accommodation of movement, and reduce the likelihood of skin marking and chafing.

Within the group of laminates of the kind often used for diaper components, greater extensibility may translate to greater pliability, as a result of reducing material thickness and/or density. Accordingly, it may be desirable that the extensible zone of fastening member 50a, be formed of a material, for example, a stretch laminate, having a relatively high extensibility. Examples of stretch laminates that may be suitable for forming an extensible zone are described in PCT Applications No. WO 2005/110731 and Published U.S. Application Nos. US 2004/0181200 and US 2004/0193133. Increasing extensibility also may enable conservation of material, in that comparatively less of a comparatively more extensible material, is required to provide a desired stretched width to the fastening member. It may be desirable, therefore, that the overall extensibility of a fastening member, expressed in terms of the ratio of the amount of extension in width over unstretched width, in response to a given lateral force load, be at least about a particular amount.

Figure 4:
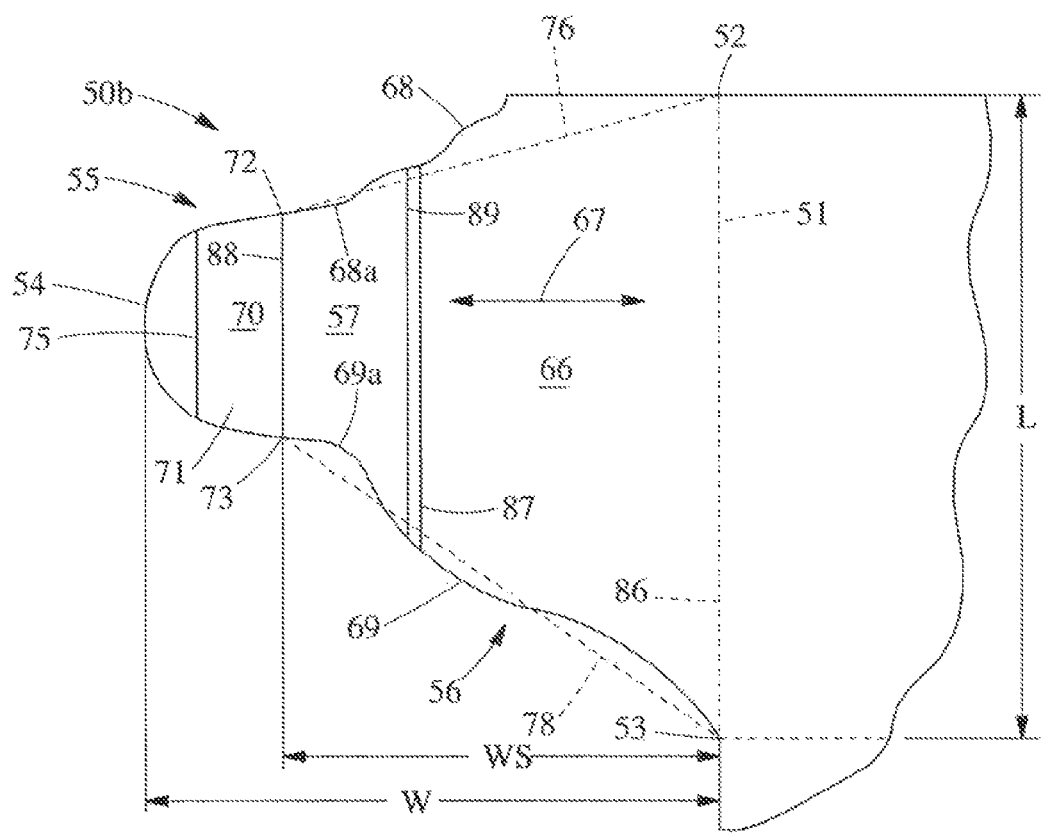
FIG. 4 is a depiction of an example of a fastening member, laid flat and viewed from above.

For example, referring to FIGS. 3 and 4, a reference width WS can be identified, as the width of the fastening member from inboard extensible zone extent 86 to fastener zone inboard edge 88. It may be desirable for the fastening member to be extensible under a laterally-applied tension load of 8.0 N to at least about 40%, or at least about 50%, or even at least about 60%, where the percentage is calculated as [(amount of extension of width WS at 8.0 N lateral tension load)/(unstretched width WS at zero lateral load)]×100%. For purposes herein, this expression of extensibility is referred to as "overall extensibility under load".

Figure 5:
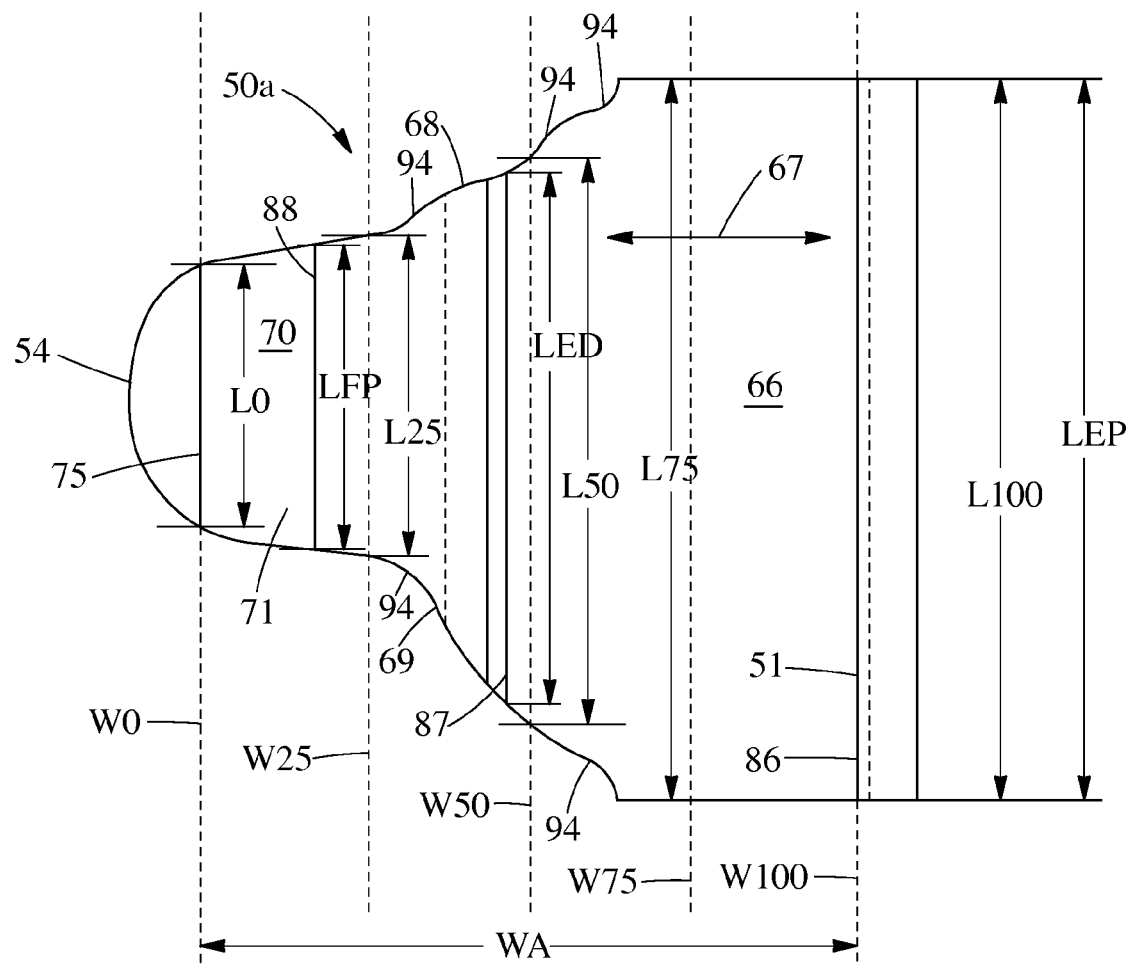
FIG. 5 is a depiction of an example of a fastening member, laid flat and viewed from above.

The desirable amount of extensibility may, however, also vary in relation to the length of the fastener zone 71 and/or the length of the extensible zone 66. In FIG. 5, the length of the fastener zone inboard edge is shown as LFP, and the length of the inboard extensible zone extent 86 is shown as LEP.

Referring to FIGS. 3 and 5, it may be desirable that the fastening member be extensible under a laterally-applied tension load of 2.1 N/cm-LFP (2.1 N per each cm fastener inboard edge length LFP) to at least about 45%, or at least about 55%, or even at least about 65%, where the percentage is calculated as [(amount of extension of width WS at 2.1 N/cm-LFP lateral tension load)/(unstretched width WS at zero load)]×100%. For purposes herein, this expression of extensibility is referred to as "extensibility under load per fastener zone length".

Still referring to FIGS. 3 and 5, it may be desirable that the fastening member be extensible under a laterally-applied tension load of 1.0 N/cm-LEP (1.0 N per each cm extensible zone inboard edge length LEP) to at least about 45%, or at least about 55%, or even at least about 65%, where the percentage is calculated as [(amount of extension of width WS at 1.0 N/cm-LEP lateral tension load)/(unstretched width WS at zero load)]×100%. For purposes herein, this expression of extensibility is referred to as "extensibility under load per extensible zone length".

For purposes of the description herein, a "highly extensible fastening member" is any fastening member having an extensibility value approximately equal to or exceeding any of the lowest overall extensibility under load, extensibility under load per fastener zone length, or extensibility under load per extensible zone length, described above.

At the same time, it may be desirable that a fastening member 50a be maximized in length L (the length of junction line 51) and surface area, to the extent feasible, for three reasons: first, to distribute the normal forces acting against the skin over a greater skin area, for greater comfort and less likelihood of skin marking and chafing; second, to distribute tension forces along a longer portion of the chassis in the waist region, thus minimizing the likelihood of tearing at the chassis; and third, to maximize skin coverage at the hips, for purposes of appearance of the diaper.

Thus, extensibility, pliability and fastening member length/surface area are several (among a number of) variables which may be adjusted to affect comfort and performance. Adjustment of these variables, however, may have undesirable effects. For example, increasing length L and surface area of the fastening member 50a, increases the likelihood that top or bottom edges of the panel region 56 may buckle and flip away from the wearer while the diaper is being worn, detracting from the appearance of the diaper and compromising some of the benefits of the increased length and surface area. Referring to FIG. 3, without intending to be bound by theory, it is believed that first and second line segments 76, 78 approximately show longitudinally outermost lines of tension in the fastening member between first and second longitudinally outermost junction points 52, 53 and first and second inboard fastener zone corners 72, 73, that would exist absent shape features of fastening element 50a discussed in more detail below. Without intending to be bound by theory, it is believed that, as stress is distributed through an extensible web material when it is stretched under lateral load as in the configuration shown in FIG. 3, material proximate to line segments 76, 78 may be subject to varying levels of longitudinally inwardly-directed, transmitted longitudinal force components, which may tend to pull material outside line segments 76, 78 longitudinally inwardly. In designs not having features herein described, this may cause the material forming the panel region 56 and/or the extensible zone 66 to buckle and even flip away from the wearer, approximately along the longitudinally outermost lines of tension. As a result of such buckling and/or flipping, normal forces in the fastening member acting on the skin may be distributed over less skin area, and appearance of the diaper may be compromised. Increasing the pliability of the fastening member material may lessen its ability to resist such buckling/flipping, and may thereby exacerbate the problem.

In addition, without intending to be bound by theory, it is believed that increasing the length L and/or pliability of fastening member 50a may increase a tendency to cause longitudinally inward-directed longitudinal force components to be distributed through the fastening member so as to act in concentrated areas along the longitudinally outer edges of the fastener zone 71. This effect, coupled with movements by the wearer that may urge the fastener zone 71 to flex such that its longitudinally outer edges move away from the wearer, may cause the longitudinal forces to be directed so as to further urge the edges of fastener zone 71 away from the wearer. As a result, the edges of the fastener zone 71 may be urged away (dish) from the landing zone to which fastener 70 is attached, which in turn, may cause the hold of the fastener 70 to the landing zone to be weakened, or even to fail.

The problems identified above may be mitigated by the use of materials having a higher planar bending stiffness for, e.g., the panel region 56, extensible zone 66, end region 55, fastener zone 71, and areas between/around them. As these areas are stiffened, the likelihood of undesired buckling of the extensible zone, and lifting of edges of the fastener zone, is decreased. This approach, however, may have undesirable effects. Stiffening the panel region 56 and/or extensible zone 66 may necessarily require using materials that are thicker and/or more dense, and add material cost. Stiffer material in panel region 56 and/or extensible zone 66 may undesirably feel less soft, supple and cloth-like to the applier and the wearer. It also may be less extensible. A reduction in extensibility in a fastening member means that, unless snugness and comfort of the article are to be compromised, features imparting lateral extensibility about the waist must be incorporated into other components of the diaper, for example, the waist regions 11, 13 of the chassis 10. Excessively increasing stiffness in the fastener zone 71 may create the feel of an unyielding object against the diaper at the wearer's abdomen, and may be a source of discomfort for the wearer, particularly when the wearer is sitting and/or bending forward at the hips. Increasing stiffness in the fastener zone also may necessitate increasing material thickness and/or density, adding cost.

Other approaches, however, may be employed.

As noted, FIGS. 3 and 4 depict examples of a fastening member, 50a and 50b. Potentially advantageous features in these examples will now be described. (FIG. 3 depicts a fastening member 50a comprising discrete components as may be attached to a wearable article; FIG. 4 depicts a fastening member 50b comprising components integral with components of a wearable article.)

A fastening member may be integrally-formed. "Integrally-formed," for purposes herein and with respect to a fastening member having a fastener attached thereto, means a fastening member that has one or both of the following characteristics: (1) It has no inboard- and longitudinally inward-pointing vertex lying along its first or second outermost lateral edges, and lying between the inboard edge of the fastener zone and a junction line; and/or (2) there is at least one longitudinal line along the end region, along which a layer of material forming the end region is longitudinally coextensive with, or longer than, a layer of material forming an extensible zone. These characteristics structurally and functionally distinguish a fastening member having one or both of them from a fastening member having a "tape" type construction, in which a comparatively short tab member, bearing a fastener and forming the end region of the fastening member, joins a relatively longer side panel region of the fastening member, in which such vertices are present and no such line exists.

Without intending to be bound by theory, it is believed that an integrally-formed fastening member is substantially less prone to buckling/flipping in the panel region and/or extensible zone as described above, as compared with possible constructions not having these characteristics.

Thus, referring to FIGS. 3, 4 and 9, for example, a layer of material in whole or in part forming end region 55, such as first surface layer 62 or second surface layer 63 may also form a part of panel region 56 and extensible zone 66. It can be appreciated that there may be at least one line (in the example depicted, there are more than one), along which an end region layer of material (such as first surface layer 62, second surface layer 63 and/or reinforcing layer 61) may be longitudinally coextensive with, or longer than, a layer of material forming the extensible zone 66. In FIGS. 3 and 4 it can be seen that one or both of outermost lateral edges 68, 69 can be shaped so as to have no inboard- and longitudinally inward-pointing vertices lying therealong, between the inboard edge 88 of the fastener zone 71 and a junction line 51. It can also be appreciated that, even where end region 55 is formed of materials or components that are discrete from materials forming panel region 56, which are affixed to an outboard portion of panel region 56, when end region 55 is appropriately shaped there still may be at least one line along which an end region layer of material may be longitudinally coextensive with, or longer than, a layer of material forming the extensible zone 66, and/or, one or both of outermost lateral edges 68, 69 can be shaped so as to have no inboard- and longitudinally inward-pointing vertices lying therealong, between the inboard edge 88 of the fastener zone 71 and a junction line 51, thus forming an integrally-formed fastening member.

While an integrally-formed fastening member may be less prone to panel region buckling and flipping, the construction may cause transfer of longitudinal forces outboard along the fastening member, toward and into the end region. Unless these forces are managed by other features, integrally-formed construction may, in some circumstances, lead to increased likelihood of fastener zone dishing.

Additional possible advantageous features of a fastening member outer shape may be identified in FIGS. 3 and 4. It can be seen that one or both of the first and second longitudinally outermost lateral edges 68, 69 may be given a profile that traverses line segments 76, 78. This feature may provide certain advantages. Without intending to be bound by theory, it is believed that it serves to direct lines of tension, and longitudinal force components thereof, away from the lateral edges and toward the longitudinal middle of the fastening member, thus further reducing the likelihood of buckling/flipping in the panel region and/or extensible zone. It also is believed such direction of longitudinal force components toward the longitudinal middle decreases the leverage such longitudinal force components may otherwise exert at the lateral outer edges of fastener zone 71 that tend to urge it dish.

Adjusting other aspects of the shape of a fastening member also may be effective at reducing fastener dishing, and panel region buckling and flipping, while allowing for generous skin coverage. Referring to FIG. 5, fastening member 50a may have junction line 51, outboard end 54, fastener zone 71, fastener 70, and extensible zone 66. Extensible zone 66 may be bounded by an inboard extensible zone extent 86 and an outboard extensible zone extent 87. Extensible zone 66 may be elastically extensible between extents 86, 87 along lateral stretch direction 67. Extents 86 and 87 may be, in one example, lines along which activation of a stretch laminate forming fastening member 50a begin and end, such that fastening member 67 is substantially elastically extensible in extensible zone 66, but not substantially elastically extensible in the areas inboard and outboard of extents 86 and 87, respectively.

For reference purposes, an acting width WA in an example such as depicted in FIG. 5 may be identified as the width of fastening member 50a from the fastener zone outboard edge 75, lying along longitudinal line W0, to inboard extensible zone extent line 86, lying along longitudinal line W100. Width WA may be divided into four equal portions, by longitudinal line W25 lying at 25% of acting width WA; longitudinal line W50 lying at 50% of acting width WA, and longitudinal line W75 lying at 75% of acting width WA, and bounded by lines W0 and W100. Fastening member 50a may have varying lengths L0, L25, L50, L75 and L100 measurable along lines W0, W25, W50, W75 and W100, respectively, where they intersect with first and second longitudinally outermost lateral edges 68, 69, as shown by way of example in FIG. 5.

Without intending to be bound by theory, it is believed that progressively improved results may be achieved, that is, a combination of—(a) effectively controlled dishing of the fastener along with (b) a fastener that is large enough in contact surface area to provide effective fastening/holding capability; (c) effectively controlled buckling and foldover of the material forming the fastening member and (d) satisfactory skin coverage—may be achieved, when L0, L25 and L50 fall approximately above the following lower limits, expressed as a percentage of L100. Further, in some examples, results may be improved if L0, L25 and L50 fall approximately below the following upper limits, expressed as a percentage of L100:

|     | /L100 | |
| --- | --- | --- |
|     | Possible lower limit | Possible upper limit |
| L0  | 25%, or<br>30%, or even<br>40% | 65%, or<br>50%, or even<br>45% |
| L25 | 30%, or<br>35%, or even<br>40% | 60%, or<br>55%, or even<br>50% |
| L50 | 50%, or<br>60%, or even<br>65% | 100%,<br>90%, or even<br>70% |

Still referring to FIG. 5, other possible characteristics of the shape of a fastening member 50a can be seen. Outermost lateral edges 68, 69 each may have profiles defining one or more inflection points 94, at which the direction of curvature of the profile changes. Without intending to be bound by theory, it is believed that including at least one such inflection point 94 on at least one of outermost lateral edges 68, 69 approximately between lines W25 and W50 is effective for diffusing longitudinal force components away from such edge, so as to reduce the likelihood of dishing of a fastener zone. Inclusion of several inflection points 94 may increase the effect. Thus, inflection points 94 may be included approximately between lines W25 and W50 on each of outermost lateral edges 68, 69. Inflection points may also be included on one or both of outermost lateral edges 68, 69 approximately between lines W50 and W75. Additional inflection points 94 may be added, as shown by way of example in FIG. 5 along first outermost lateral edge 68, suggesting two inflection points 94 approximately between lines W25 and W50, and two inflection points 94 approximately between lines W50 and W75.

Still referring to FIG. 5, without intending to be bound by theory, it is also believed that, where the fastener comprises or is disposed on a patch of material that adds stiffness to the fastener zone 71, there is an effective relationship between the fastener zone inboard edge length LFP, extensible zone outboard edge length LED (measured along outboard extensible zone extent 87), and extensible zone inboard edge length LEP (measured along inboard extensible zone extent line 86). It is believed that chances of minimizing fastener dishing and buckling/flipping of the panel region 56 may be enhanced when LFP lies within a range from about 50% to about 75%, or from about 55% to about 75%, or from about 60% to about 75%, of LED. It is also believed that chances of minimizing fastener dishing and buckling/flipping of the fastening member 50a may be enhanced when LFP lies within a range from about 35% to about 65% of LEP, or about 40% to about 50% of LEP, or even about 40% to about 45% of LEP.

Figure 6:
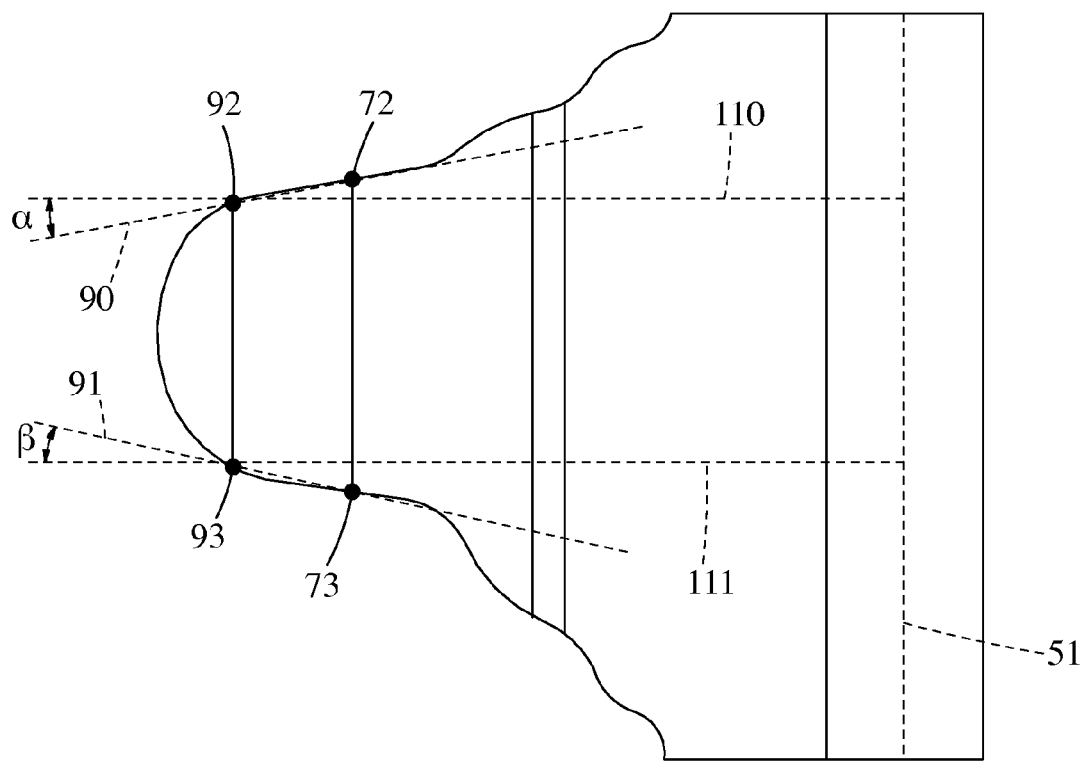
FIG. 6 is a depiction of an example of a fastening member, laid flat and viewed from above.

Additional features are apparent from FIGS. 3-6, and may be helpful to reduce the likelihood of panel region buckling/flipping and/or fastener zone dishing. Referring specifically to FIG. 5, it can be seen that L0 (which corresponds to the length of the outboard edge 75 of fastener zone 71) may be less than LFP (which corresponds to the length of the inboard edge 88 of fastener zone 71). Outboard fastener zone corners 92 and 93 are respective points on lateral edges 68, 69 intersected by fastener zone outboard extent 75. Referring to FIG. 6, first and second fastener zone lateral edge lines 90, 91 may be identified, which connect first inboard fastener zone corner 72 with first outboard fastener zone corner 92, and second inboard fastener zone corner 73 with second outboard fastener zone corner 93, respectively. As a result of differing lengths of L0 and LFP (see FIG. 5), referring to FIG. 6, angles α and β are formed by the intersection of lateral edge lines 90, 91 and lateral lines 110, 111 that are perpendicular to junction line 51 as shown. For purposes herein, these angles α and β are referred to as "fastener zone lateral edge angles." Without intending to be bound by theory, it is believed that shaping the fastening member such that these fastener zone lateral edge angles α and β lie between about 0 degrees and about 30 degrees, or between about 2 degrees to about 20 degrees, or between about 2 degrees to about 15 degrees, or even between about 5 degrees and 15 degrees, extending outwardly from the lateral lines 110 and 111, substantially helps reduce the likelihood of fastener zone dishing as a result of the effects of distributing force components within the fastening member, across the fastener zone. Angles α and β need not be the same. They may be the same, or they may be different. One or both may fall within one or more of the ranges set forth above.

Referring again to FIG. 5, for purposes of best positioning of a fastener relative to the location at which an applier is likely to grasp the fastening member, it may be desirable to locate fastener 70 such that it lies entirely outboard of line W25.

For purposes of minimizing the cost of a fastening member, it may be desirable to make it as narrow in lateral width as practical, so as to conserve material. However, it may also be desirable to provide for sufficient width of the fastening member as the article is applied to a wearer. Referring to FIG. 5, it is believed, therefore, that imparting extensible zone 66 with an unstretched extensible zone width (i.e., the distance between inboard and outboard extensible zone extents 86, 87 when extensible zone 66 is not stretched) that exceeds about 50% of the acting width WA, is effective to satisfy these conflicting purposes. At the same time, in the interest of controlling force transmission to the fastener zone, it may be undesirable for the unstretched extensible zone width to exceed about 75 percent of the acting width WA. Thus, it may be desirable that the extensible zone 66 have a width from about 50 percent to about 75 percent of the acting width of the fastening member. It also may be desirable that outboard extensible zone extent 87 be located between W25 and W50.

As noted, the design of an integrally-formed fastening member may in some circumstances promote transfer of longitudinal force components to the edges of the fastener zone. This may urge the fastener to dish, and, as a result, pop off (suddenly and entirely disengage from) its associated landing zone when in use. For this reason, utilizing a combination of fastener and landing zone material ("fastening combination") that exhibits a good resistance to pop-off may be desired.

A test denominated herein the Vertical Pull Test has been devised as a relative indicator of the performance of a fastening combination in use. The Vertical Pull Test measures the force and work, over separation distance, necessary to separate engaged flat samples of fastener and landing zone material, in a direction orthogonal to the plane along which the engaged samples lie, after the samples have been engaged with a given force and then displaced relative each other in a direction parallel to such plane (i.e., a shear direction), as a condition of the test. Without intending to be bound by theory, it is believed that this Shear Displacement, at least in part, simulates an engagement condition such as that which occurs when a hook-type fastener on a fastening member is engaged with a landing zone (including the loops component, of a hook-and-loop fastening system) on a wearable article when it is applied to a wearer, in that, following engagement of the fastener with the landing zone, tension in the fastening member pulls the fastener across the landing zone slightly (in a shear direction), resulting in a relative displacement along the shear direction between the two components. When the fastener comprises a patch of hooks and the landing zone material comprises an associated loops component, a shear displacement affects the interaction of the hooks and loops components. For example, following a shear displacement, loops on the loops component may be caught, gathered and engaged in greater numbers, or engaged more tightly, about hooks, or the loops may be stretched, separated from their substrate, or broken in some number, etc.; while the hooks may be deformed to some extent from their relaxed shapes and orientations.

In order to reduce the likelihood that a hooks-type fastener will pop off a landing zone when in use, it may be desirable to select a combination of fastener and landing zone material that exhibits a Vertical Peak Load and Greatest Vertical Load at a given Displacement and/or combinations thereof as set forth below. (Herein, these terms have meanings as described in the description of the Vertical Pull Test, below; "Displacement" refers to the distance of separation of the components of a fastening combination following engagement, orthogonal to the plane of engagement; and "Shear Displacement" refers to the distance by which the samples are displaced in a shear direction along the plane of engagement, before the vertical pulling portion of the test commences.)

Merely because a fastening combination may sustain a given load orthogonal to the plane of engagement before separating, does not mean that the combination will be satisfactorily resistive to pop-off. Through use of the Vertical Pull Test described herein, it has been found that some examples of fastening combinations may exhibit a relatively brittle engagement, meaning that, once a particular Displacement is reached at the combination's Vertical Peak Load, exceeding that Displacement causes the vertical load sustained by the combination to drop relatively quickly to zero—in other words, the fastening combination appears to suddenly "let go", or "pop" apart. Without intending to be bound by theory, it is believed that, if the Vertical Peak Load that these examples can sustain is not sufficiently high, they can be relatively, unsatisfactorily susceptible to pop-off when placed in their intended use.

On the other hand, other examples of fastening combinations may have a relatively more elastic or tenacious engagement, meaning that, once a particular Displacement is reached at the combination's Vertical Peak Load, exceeding that Displacement does not cause the vertical load sustained by the combination to drop as quickly to zero—in other words, the fastening combination continues to resist separation, and exhibits a load sustaining capability, after Displacement at Vertical Peak Load is exceeded, that is relatively greater than the capability of the examples described in the preceding paragraph.

Without intending to be bound by theory, it is believed that, in a comparison between two fastening combinations having equal Vertical Peak Load capability as measured according to the Vertical Pull Test, the one that is less brittle, i.e., more elastic and tenacious, will be more resistive to pop-off when placed in use in a wearable article such as a disposable diaper. Without intending to be bound by theory, it is believed that this is true because the more tenacious fastening combination is better able to withstand and recover from varying forces and displacements imposed by the movements of the wearer, while the more brittle fastening combination is less able to withstand and recover from such varying forces and displacements. At the same time, however, it is believed that too much elasticity in the engagement corresponds with a loose arrangement of loops in the loops component and/or hooks that are overly loose or flexible. This results in a loose engagement that, when present on a wearable article such as a disposable diaper, makes the associated fastening member susceptible to being caught on surrounding objects and thereby forcibly separated from the landing zone, as the wearer moves about his/her environment.

It is believed that relative brittleness and/or elasticity/tenacity of differing fastening combinations may be indicated by application of the Vertical Pull Test. Further, it is believed that fastening combinations exhibiting the following performance values in application of the Vertical Pull Test are more resistive to pop-off and/or are more tightly engaged, than fastening combinations falling outside or not exhibiting these values:

| Property/Value | (I) Vertical Pull Test @ 1 mm Shear Displacement | (II) Vertical Pull Test @ 2 mm Shear Displacement |
| --- | --- | --- |
| (A) Vertical Peak Load (N) | at least about 4.0; more preferably at least about 8.0; or even more preferably at least about 12 | at least about 5.0; more preferably at least about 15; or even more preferably at least about 20 |
| (B) Displacement at Vertical Peak Load (mm) (only in combination with other values (A), (C) and/or (D), as set forth below) | (1) at least about 0.5; more preferably at least about 1.0; or even more preferably at least about 1.5; and optionally, preferably, (2) less than about 6.0; more preferably less than about 4.0; or even more preferably less than about 2.0 | (1) at least about 0.5; more preferably at least about 1.0; or even more preferably at least about 1.5; and optionally, preferably, (2) less than about 5.0; more preferably less than about 4.0; or even more preferably less than about 3.0 |
| (C) Greatest Vertical Load between 0.0 and 0.5 mm Displacement (N) | at least about 1.5; more preferably at least about 3.0; or even more preferably at least about 4.5 | at least about 3.0; more preferably at least about 6.0; or even more preferably at least about 10 |
| (D) Greatest Vertical Load between 0.0 and 1.0 mm Displacement (N) | at least about 3.0; more preferably at least about 5.0; or even more preferably at least about 8.0 | at least about 4.0; more preferably at least about 8.0; or even more preferably at least about 12 |

Additionally, without intending to be bound by theory, it is believed that a fastening combination exhibiting one or more combinations of the values (A)-(D) set forth in the table above will be more resistive to pop-off during use, than a fastening combination not exhibiting such combination of values. Thus, for example, a fastening combination may exhibit one of the following combinations of values from Column I above, when tested at a 1 mm Shear Displacement:

A fastening combination exhibiting both
(A) a Vertical Peak Load of at least about 4.0N, more preferably at least about 8.0N, or even more preferably at least about 12N; and
(C) a Greatest Vertical Load between 0.0 and 0.5 mm Displacement of at least about 1.5N, more preferably at least about 3.0N, or even more preferably at least about 4.5N,
in the Vertical Pull Test at a 1 mm Shear Displacement would be expected to be more resistive to pop-off than a fastening combination not exhibiting such combination of values.

A fastening combination exhibiting both
(A) a Vertical Peak Load of at least about 4.0N, more preferably at least about 8.0N, or even more preferably at least about 12N; and
(D) a Greatest Vertical Load between 0.0 and 1.0 mm Displacement of at least about 3.0N, more preferably at least about 5.0N, or even more preferably at least about 8.0N,
in the Vertical Pull Test at a 1 mm Shear Displacement would be expected to be more resistive to pop-off than a fastening combination not exhibiting such combination of values.

A fastening combination exhibiting
(C) a Greatest Vertical Load between 0.0 and 0.5 mm Displacement of at least about 1.5N, more preferably at least about 3N, or even more preferably at least about 4.5N; and
(B)(1) a Displacement at Vertical Peak Load of at least about 0.5 mm, more preferably at least about 1.0 mm, even more preferably at least about 1.5 mm;
and optionally, preferably
(B)(2) a Displacement at Vertical Peak Load of less than about 6.0 mm, more preferably less than about 4.0 mm, and even more preferably less than about 2.0 mm, in the Vertical Pull Test at a 1 mm Shear Displacement would be expected to be more resistive to pop-off than a fastening combination not exhibiting such combination of values.

A fastening combination exhibiting
(D) a Greatest Vertical Load between 0.0 and 1.0 mm Displacement of at least about 3.0N, more preferably at least about 5.0N, or even more preferably at least about 8.0N; and
(B)(1) a Displacement at Vertical Peak Load of at least about 0.5 mm, more preferably at least about 1.0 mm, even more preferably at least about 1.5 mm;
and optionally, preferably
(B)(2) a Displacement at Vertical Peak Load of less than about 6.0 mm, more preferably less than about 4.0 mm, and even more preferably less than about 2.0 mm, in the Vertical Pull Test at a 1 mm Shear Displacement would be expected to be more resistive to pop-off than a fastening combination not exhibiting such combination of values.

A fastening combination exhibiting
(A) a Vertical Peak Load of at least about 4.0N, more preferably at least about 8.0N, or even more preferably at least about 12N; and
(C) a Greatest Vertical Load between 0.0 and 0.51 mm Displacement of at least about 1.5N, more preferably at least about 3.0N, or even more preferably at least about 4.5N; and
(B)(1) a Displacement at Vertical Peak Load of at least about 0.5 mm, more preferably at least about 1.0 mm, even more preferably at least about 1.5 mm;
and optionally, preferably
(B)(2) a Displacement at Vertical Peak Load of less than about 6.0 mm, more preferably less than about 4.0 mm, and even more preferably less than about 2.0 mm, in the Vertical Pull Test at a 1 mm Shear Displacement would be expected to be more resistive to pop-off than a fastening combination not exhibiting such combination of values.

A fastening combination exhibiting
(A) a Vertical Peak Load of at least about 4.0N, more preferably at least about 8.0N, or even more preferably at least about 12N; and
(D) a Greatest Vertical Load between 0.0 and 1.0 mm Displacement of at least about 3.0N, more preferably at least about 5.0N, or even more preferably at least about 8.0N; and
(B)(1) a Displacement at Vertical Peak Load of at least about 0.5 mm, more preferably at least about 1.0 mm, even more preferably at least about 1.5 mm;
and optionally, preferably
(B)(2) a Displacement at Vertical Peak Load of less than about 6.0 mm, more preferably less than about 4.0 mm, and even more preferably less than about 2.0 mm,
in the Vertical Pull Test at a 1 mm Shear Displacement would be expected to be more resistive to pop-off than a fastening combination not exhibiting such combination of values.

Similarly, a fastening combination may exhibit combinations of values analogous to those described immediately above, but from Column II in the table above, when tested at a 2 mm Shear Displacement.

Fastening combinations having one or more of these combinations of values are expected to have high enough peak load sustaining capability for wearable articles such as disposable diapers, coupled with enough tenacity in the engagement, to resist pop-off under normal conditions, and a suitably tight engagement.

Additionally, without intending to be bound by theory, it is believed that a fastening combination exhibiting a value (A), (C) or (D) as set forth in the table above that is equal to or greater for a Shear Displacement of 2 mm than for a Shear Displacement of 1 mm would be expected to be more resistive to pop-off than a fastening combination exhibiting values that do not satisfy this relationship. It is believed that a fastening combination exhibiting such a relationship of values is better able to accommodate varying shear displacements as are imposed in use by, e.g., varying sizes of wearers and/or varying tensions placed on fastening members by persons applying the associated wearable articles. Thus, for example:

A fastening combination exhibiting (A) a Vertical Peak Load of at least about 4.0N in the Vertical Pull Test at a 1 mm Shear Displacement (Column I); and (A) a Vertical Peak Load of equal to or greater than about 4.0N in the Vertical Pull Test at a 2 mm Shear Displacement (e.g., Column II), would be expected to be more resistive to pop-off than a fastening combination not exhibiting such relationship of values.

A fastening combination exhibiting (C) a Greatest Vertical Load between 0.0 and 0.5 mm Displacement of at least about 1.5N in the Vertical Pull Test at a 1 mm Shear Displacement (Column I); and (C) a Vertical Peak Load of equal to or greater than about 1.5N in the Vertical Pull Test at a 2 mm Shear Displacement (e.g., Column II), would be expected to be more resistive to pop-off than a fastening combination not exhibiting such relationship of values.

A fastening combination exhibiting (D) a Greatest Vertical Load between 0.0 and 1.0 mm Displacement of at least about 3.0N in the Vertical Pull Test at a 1 mm Shear Displacement (Column I); and (D) a Vertical Peak Load of equal to or greater than about 3.0N in the Vertical Pull Test at a 2 mm Shear Displacement (e.g., Column II), would be expected to be more resistive to pop-off than a fastening combination not exhibiting such relationship of values.

Additional examples of relationships of properties analogous to those immediately above exist, for the more preferred and even more preferred values set forth in Column I. For example, a fastening combination exhibiting (A) a Vertical Peak Load of at least about 8.0N in the Vertical Pull Test at a 1 mm Shear Displacement (Column I); and (A) a Vertical Peak Load of equal to or greater than about 8.0N in the Vertical Pull Test at a 2 mm Shear Displacement (e.g., Column II), would be expected to be more resistive to pop-off than a fastening combination not exhibiting such relationship of values . . . and so on, for the even more preferred values, and relationships of properties (C) and (D), as described immediately above.

Without intending to be bound by theory, it is believed further, that using a fastening combination exhibiting values in the Vertical Pull Test as described above may also have a synergistic effect, when combined with other features such as the shape characteristics described above and/or fastener zone Stiffness characteristics described below, with regard to avoiding undesirable fastening combination disengagement.

Increasing the Stiffness of fastener zone 71 may serve to help reduce the likelihood or extent of fastener dishing. A fastener zone 71 having a Stiffness of at least about 1,500 N/m may be helpful. As also noted above, however, effecting an excessive increase in the stiffness of fastener zone 71 may be undesirable because it may result in the feel of an unyielding object against the diaper at the wearer's abdomen, and may be a source of discomfort for the wearer, particularly when the wearer is sitting and/or bending forward at the hips. Additionally, increasing stiffness in the fastener zone may necessitate increasing material thickness and/or density, adding cost. A fastener zone 71 may be deemed too stiff under certain circumstances, for these reasons. Thus, it may be desirable to have an upper limit of, for example, 9,000 N/m, on the amount of Stiffness of the fastener zone 71 that is imparted.

At the same time, imparting a Stiffness to fastener zone 71 above some minimum value may by itself be insufficient to satisfactorily prevent dishing. Without intending to be bound by theory, however, it is believed that the shaping of fastening member 50 as described above may be unexpectedly synergistic in combination with a limited amount of Stiffness of the fastener zone 71. In other words, without intending to be bound by theory, it is believed that the shaping described above magnifies the effect of adding to the Stiffness of fastener zone 71, in reducing or preventing dishing. Accordingly, it is believed that dishing can be effectively and satisfactorily reduced or prevented if fastener zone 71 has a Stiffness of at least about 1,500 N/m, or 2,500 N/m, or 3,500 N/n, or 4,000 N/m, and the fastening member has one or more of the shape and construction characteristics identified and described herein. In order to reduce the likelihood that the fastener zone is perceived as too stiff, possibly uncomfortably so, by the wearer and/or applier, however, it may be desirable that the fastener zone has a Stiffness of no more than about 9000 N/m, or 7,500 N/m, or even 6,000 N/m.

Referring again to FIGS. 3 and 4, fastener zone 71 may overlap one or more underlying layers of materials in end region 55 which may both contribute to Stiffness of fastener zone 71, and may also extend from fastener zone 71 in an inboard direction. An intermediate region 57 may include such underlying material(s), and have its own Stiffness. If intermediate region 57 is imparted with an intermediate Stiffness that is less than the Stiffness of fastener zone 71, but greater than the Stiffness of panel region 56 and/or extensible zone 66, this may have the advantages of bearing and resisting longitudinal force components that develop within the panel region 56, and preventing their transfer to fastener zone 71, thus reducing the likelihood of dishing of fastener 70, as well as reducing the likelihood of buckling/flipping in panel region 56, without substantially compromising wearer comfort afforded by a highly-extensible, pliable panel region 56. Thus, for example, intermediate region 57, or a portion thereof, may be imparted with an intermediate Stiffness of between about 200 N/m and about 1000 N/m, or between about 300 N/m and about 750 N/m, or even between about 400 N/m and about 600 N/m. Intermediate region 57 or a portion thereof, as well as panel region 56, may be imparted with any additional Stiffness characteristics, including variations and gradients thereof, as described in co-pending U.S. application Ser. No. 11/895,169.

Figure 7:
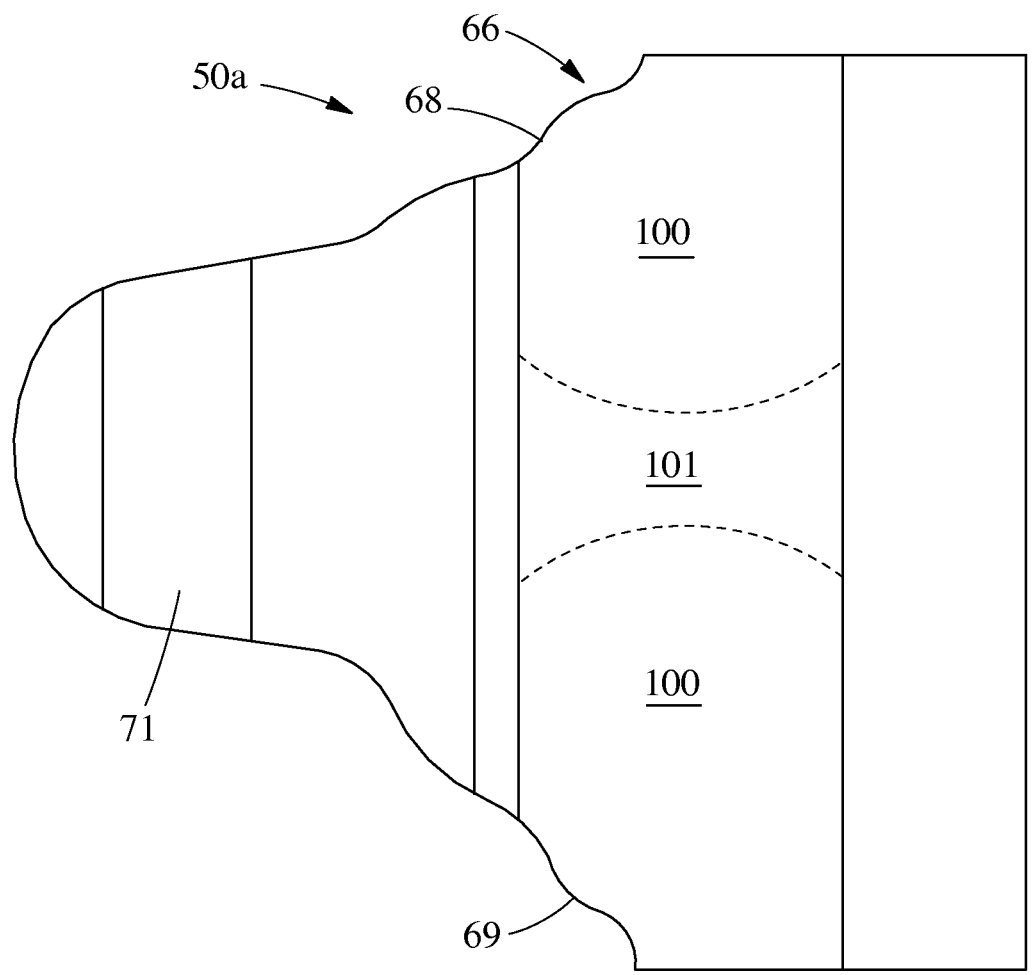
FIG. 7 is a depiction of an example of a fastening member, laid flat and viewed from above.

A fastening member may have an extensible zone 66 formed of a stretch laminate that has been activated by monoaxial stretching of the section of the laminate which contains the laminated-in elastomeric material layer 64, or a portion thereof, in a manner described in more detail, for example, in U.S. Pat. No. 4,834,741, and in published PCT applications Nos. WO 1992/015446 and WO 1992/015444, which are incorporated herein by reference. In addition, extensible zone 66 may include force-focusing features such as described in U.S. Published Application No. 2007/0142815. Referring to FIG. 7, a fastening member 50a may have an extensible zone 66 having regions of varying moduli of elasticity. For example, extensible zone 66 may have a relatively higher modulus region 101, and relatively lower modulus regions 100 as suggested. High modulus region 101 may be disposed at or about the longitudinal center of extensible zone 66 as suggested in FIG. 7, or may be disposed at other locations. In the example suggested in FIG. 7, however, relatively high modulus region 101 will bear a greater proportion of lateral tension forces per surface area, thus "focusing" lateral tension forces toward the longitudinal center of the fastening member. Without intending to be bound by theory, it is believed that, as a result, stresses acting along longitudinally outermost edges 68, 69 are reduced while overall lateral tension in the fastening member is maintained such that the article maintains good fit, while likelihood of fastener zone dishing may be reduced. Other examples of materials including zones of differing moduli are described in, for example, PCT Application Nos. WO 2007/069227 and WO 2008/084449.

Figure 8:
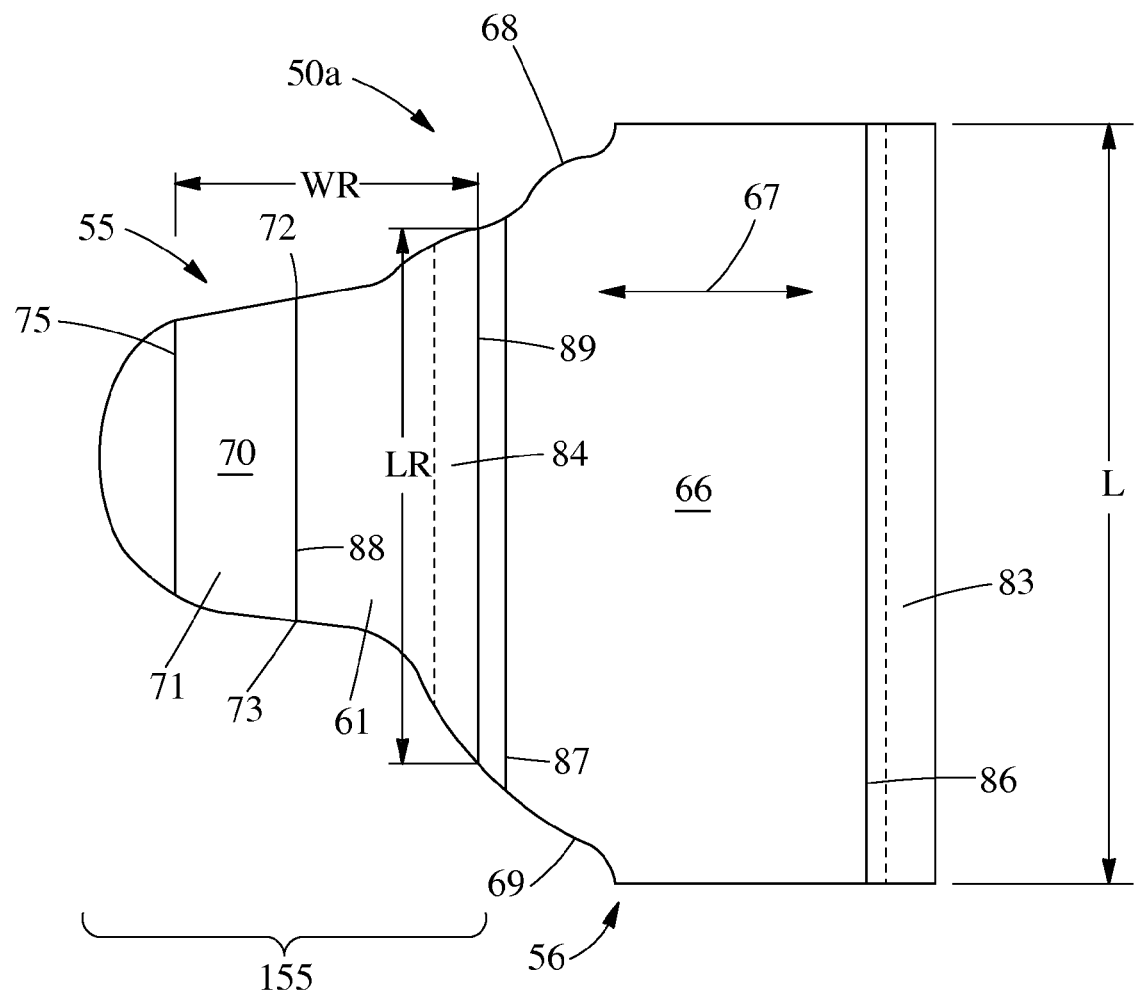
FIG. 8 is a depiction of an example of a fastening member, laid flat and viewed from above.

In addition to being relatively more prone to buckling/flipping, a relatively highly extensible, more pliable material may be less robust, and have less resistance to tearing. This may become an issue, for example, when an applier tugs on end region 55 in order to apply the diaper to a wearer. If the applier tugs with sufficient lateral force, material forming panel region 56 may tear, particularly at locations where stress concentrates, such as, for example, where the fastening member shortens to an end region and/or a discontinuity in fastening member construction results in an abrupt transition from relatively more pliable portion of the fastening member to a relatively stiffer portion of the fastening member. Referring to FIG. 8, in one example, fastener zone 71 may comprise a patch of material which, when affixed to a substrate, creates a combination of the patch material and the substrate having greater stiffness than that of adjoining substrate alone. Thus, when fastening member 50a is loaded under lateral tension along stretch direction 67, stresses may concentrate along fastener zone inboard edge 88. Additionally, where, as in the example depicted in FIG. 8, the fastener 70 may occupy a shortened end region, stresses may be especially concentrated in the substrate along first and second longitudinally outermost lateral edges 68, 69, at first and second inboard fastener zone corners 72, 73. As the manufacturer increases the amount of stretch and/or pliability for the selected material forming panel region 56 by reducing basis weight, the likelihood of tearing at first and/or second inboard fastener zone corners 72, 73 may increase.

In order to improve the ability of the fastening member to withstand and/or diffuse such stress concentrations and reduce the likelihood of such tearing, the manufacturer may form end region 55 of a material or combination of materials that has greater tensile strength at least in the lateral direction, or in several directions, than the material(s) forming the extensible zone. As another option, the manufacturer may add a reinforcing layer to end region 55 to form a laminate section at end region 55 having greater tensile strength in at least the lateral direction, or in several directions, than the material(s) forming the extensible zone. Either approach may be used to form a strengthened end region 155. (For purposes of this description, "strengthened," with respect to an end region of a fastening member, means an end region that has greater tensile strength in at least the lateral direction, than the material(s) forming the extensible zone).

FIG. 9 schematically depicts a simplified lateral, exploded cross section of one example of a fastening member 50a having a strengthened end region 155. As shown in FIG. 9, a fastening member 50a may have an extensible zone 66 between inboard and outboard extensible zone extents 86, 87, an inextensible inboard zone 83, and an inextensible end region 55. A fastening member 50a may be constructed in several layers and may have one or two surface layers 62, 63, which may consist of a nonwoven material, and an elastomeric material layer 64 laminated to and/or between the one or two surface layers 62, 63, to form a stretch laminate. Suitable examples of stretch laminates and elastomeric films for forming panel region 56 and/or extensible zone 66 include those described in copending U.S. Published Application No. US 2007/0293111. The one or two surface layers 62, 63 may be wider along stretch direction 67 than the elastomeric material layer 64, and may be bonded together in regions forming end region 55 and inboard zone 83. The inboard zone 83 may be formed of only the two surface layers 62, 63 bonded together. The end region 55 may be reinforced by a reinforcing layer 61 having reinforcing layer inboard edge 89, thereby forming strengthened end region 155. Reinforcing layer 61 may be disposed in an overlapping zone 84, in overlapping relationship with elastomeric material layer 64. The width of the reinforcing layer 61 and/or the width of the elastomeric material layer 64 may be adjusted so that their edges overlap to form an overlapping zone 84 of desired width. The reinforcing layer 61 may be formed of, for example, a nonwoven material. Inclusion of reinforcing layer 61 may be used to impart greater tensile strength in at least the lateral direction, to end region 55, than it would have absent a reinforcing layer. The reinforcing layer 61 may be disposed between the surface layers 62, 63 and beneath the elastomeric material layer as suggested in FIG. 9, or may be disposed between the surface layers 62, 63 and above the elastomeric material layer, or on the outside surface of either of surface layers 62, 63. In another example (not shown), strengthened end region 155 may comprise one layer, or a plurality of layers of material forming a laminate, that is discrete from material forming panel region 56, bonded at its inboard edge to the outboard edge of an adjoining material forming panel region 56 and/or extensible zone 66, or component thereof. A fastener 70 may be affixed to an outside surface of strengthened end region 155. Fastener 70, and layers 61, 62, 63 and 64 may be laminated together in a laminate structure, by any suitable adhesive and/or other bonding laminating technique(s). Reinforcing layer 61 and/or strengthened end region 155 may be formed of materials selected so as to impart, or contribute to imparting, a desired amount of Stiffness to fastener zone 71 and/or intermediate region 57, as described above.

In the example depicted in FIG. 9, the extensible zone 66 may be narrower in width than the elastomeric material layer 64, and end at a location inboard of the overlapping zone 84, providing a relatively inelastic portion including overlapping zone 84, for anchoring the reinforcing layer 61 to elastomeric material layer 64 and transitioning to the strengthened end region.

Referring again to FIG. 8 and FIG. 9, reinforcing layer 61 may be sized so as to extend from end region 55 in an inboard direction to form strengthened end region 155, ending on the inboard side at reinforcing layer inboard edge 89. Reinforcing layer 61 may have a length LR along its inboard edge 89 extending between first and second longitudinally outermost lateral edges 68, 69, and a width WR from the fastener zone outboard edge 75 to reinforcing layer inboard edge 89.

In order to ensure an acceptable level of consumer satisfaction with its product, the manufacturer may wish to design and manufacture fastening member 50a so that it will sustain a particular lateral tension load before any failure in the material from tearing, delamination/separation, breaking of bonds, etc. For fastening members of the type that may be used on diapers, the manufacturer may require and design fastening members to sustain, for example, at least 18 N, 24 N, 30 N or even 34 N of lateral peak tension load before failing, when pulled at a speed sufficient to accomplish a strain rate in the extensible zone of between about 5 seconds$^{-1}$ to about 40 seconds$^{-1}$. The weakest location of a particular material forming panel region 56 may be, for example, along its longitudinally shortest dimension, i.e., the point at which the smallest longitudinal cross section of material is subject to the stress required to sustain the lateral load (without support from any stiffening or reinforcing layer). In some examples such as depicted in FIGS. 8 and 9, and in which a stretch laminate is activated as described above, surface layers 62, 63 may be laterally weakened in the activation process. Thus, in the example depicted in FIG. 8, the weakest portion of fastening member 50a might in some circumstances be along reinforcing layer inboard edge 89, or along, for example, outboard extensible zone extent line 87—at which a combination of activation-weakened material and relatively small longitudinal dimension of extensible zone 66 exists. Accordingly, when a strengthened end region 155 of a fastening member 50a having a layered construction as depicted in FIG. 9, is desirably sized, failure of materials forming the fastening member 50a under lateral loading might be expected to occur, on average, at a location proximate to the strengthened end region/reinforcing layer inboard edge, rather than elsewhere on the fastening member. It will be appreciated that a width for a reinforcing layer 61 or a strengthened end region 155 that substantially exceeds this desirably-sized value may compromise the extensibility of the fastening member, reduce the width of the extensible zone, or may be unneeded to provide the required design strength, and thus, add unnecessary material cost, while a width less than this value may increase the likelihood of failure under a lateral load below the intended design load.

Thus, in the examples depicted in FIG. 8 and FIG. 9, reinforcing layer 61 may be sized so as to have an affixed width WR overlapping and affixed to other layer(s) in overlapping zone 84, and so that its affixed inboard edge 89 (and thus, the inboard edge of strengthened end region 155) lies along a line at which the affixed length along inboard edge 89 is of a length LR that is from about 66 percent to about 80 percent, or from about 69 percent to about 77 percent, or even from about 71 percent to about 75 percent, of the length L of the fastening member along junction line 51. Without intending to be bound by theory, it is believed that a reinforcing layer/strengthened end region sized within one or more of these ranges desirably bears and/or reduces stress concentrations about the fastener zone when the fastening member is under lateral tension load, and achieves a satisfactory balance between minimizing the likelihood that the fastening member will tear under lateral loading in an amount less that its intended design provides, while at the same time minimizing added material costs resulting from inclusion of a strengthened end region.

Other types, and methods of making, a strengthened end region, are described in, for example, PCT Applications Nos. WO 2003/039426 and WO 2004/082918.

Figure 10A:
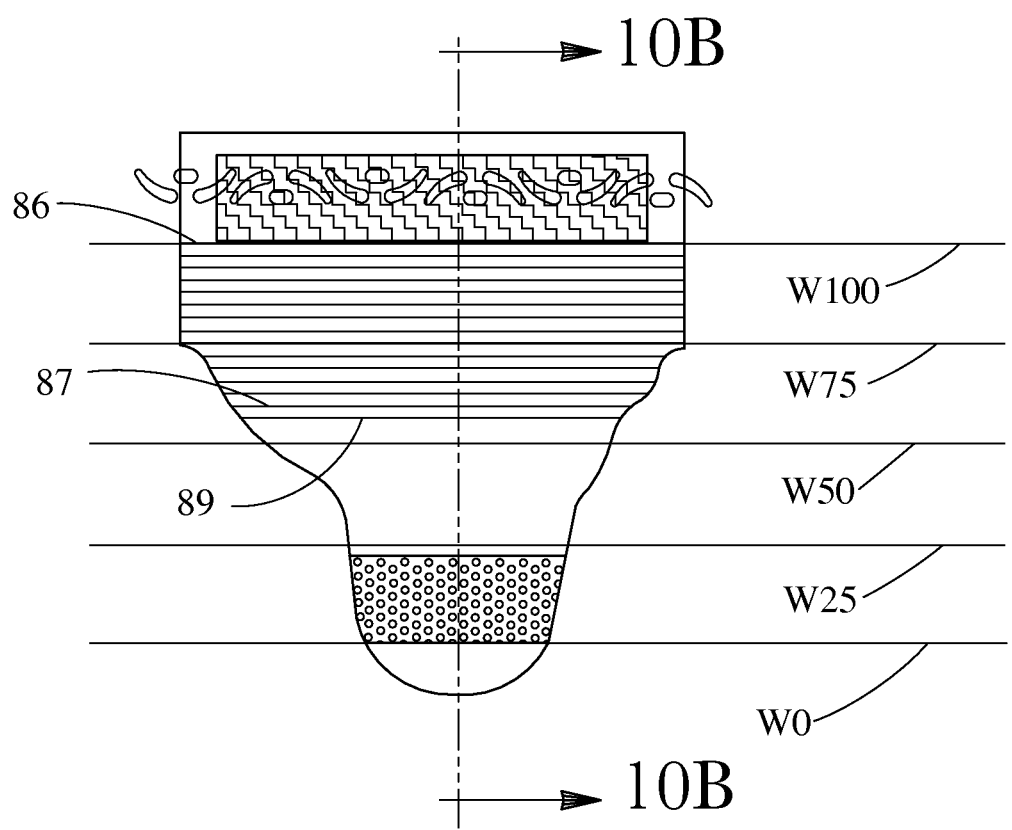
FIG. 10A is a reproduction of a CAD drawing depicting an example of a fastening member, laid flat and viewed from above.
Figure 10B:
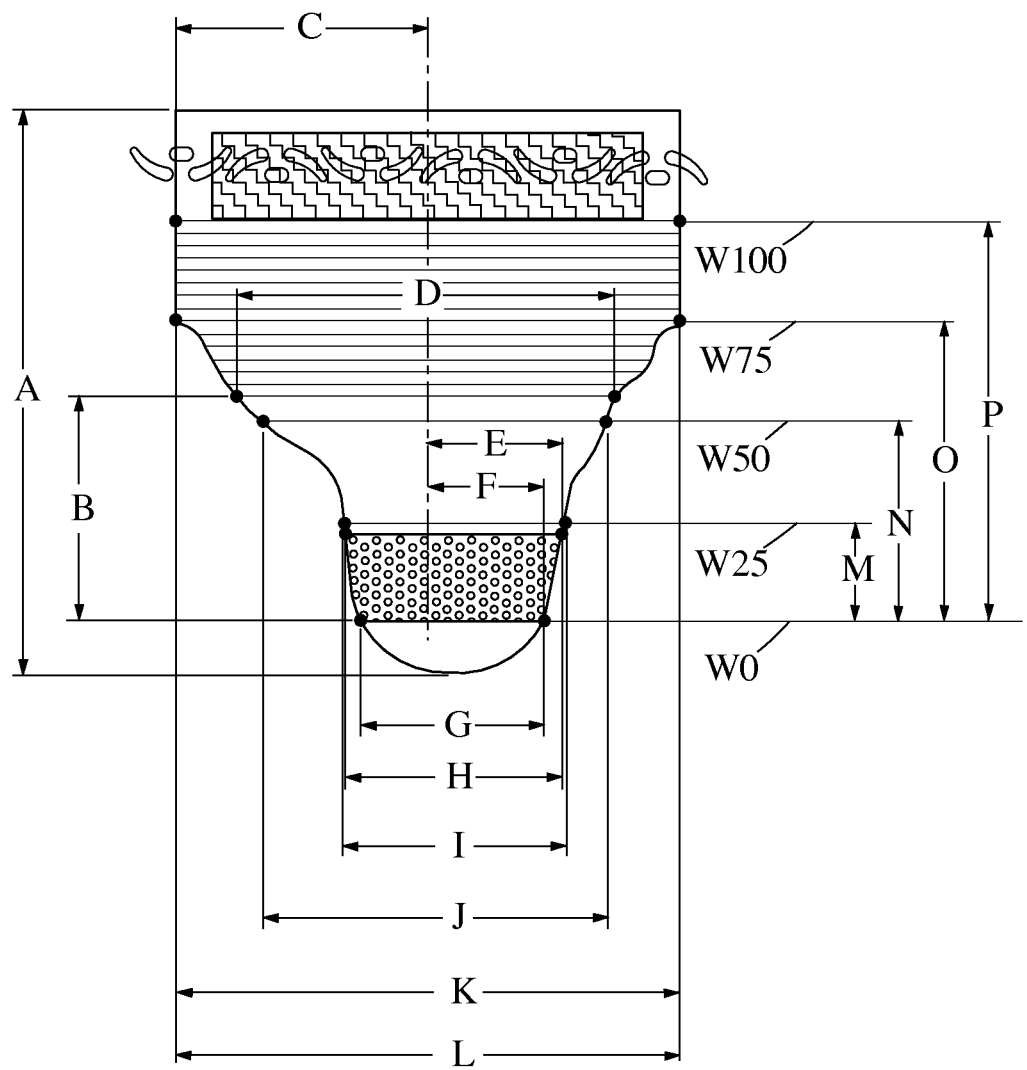
FIG. 10B is a reproduction of a CAD drawing depicting an example of a fastening member, laid flat and viewed from above.
Figure 10C:
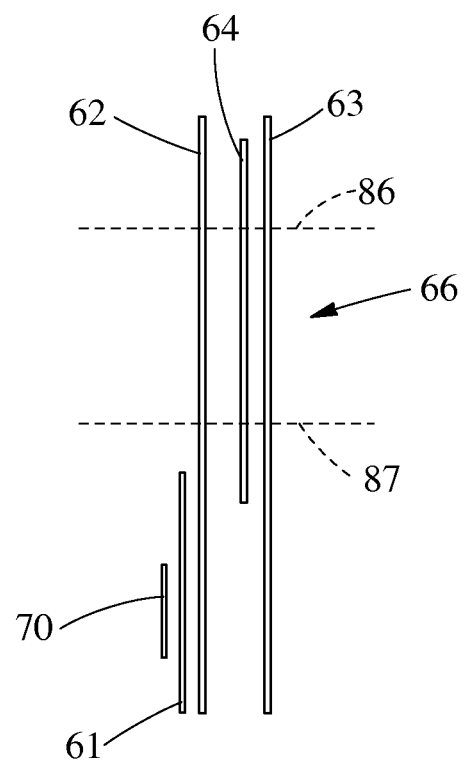
FIG. 10C is a depiction of a simplified schematic, exploded lateral cross section through the example of the fastening member depicted in FIG. 10A.

In order to manufacture a fastening member having the features described herein, a member having the shape and dimensions shown in FIG. 10A might be cut from a suitable combination laminate, having the layers shown in FIG. 10B. All numerical values shown in FIG. 10A are in millimeters. (The drawing is not to scale.) In cross section the exemplary fastening member may have the general layered configuration depicted in FIG. 10B. The laminate assembly from which the fastening ear might be cut, including first surface layer 62, elastomeric material layer 64, second surface layer 63 and reinforcing layer 61 might be formed of materials as follows:

| Layer | Material |
|---|---|
| Fastener 70 | APLIX 963, available from Aplix Fastener UK Ltd., Suffold, England |
| Adhesive (between fastener 70 and reinforcing layer 61) | hot melt adhesive, BOSTIK H2988F01, available from Bostik, Middleton, MA, applied at about 150 gsm (grams per square meter) |
| Reinforcing Layer 61 | 40 gsm monolayer spunbond polypropylene nonwoven, PROWEB, available from Rheinische Kunststoffwerke, Gronau Germany |
| Adhesive (between reinforcing layer 61 and first surface layer 62) | hot melt adhesive, BOSTIK H2511, available from Bostik, Middleton, MA, applied at about 40 gsm |
| First Surface Layer 62 | 31 gsm high elongation carded (HEC), point-bonded nonwoven, FPN 332D available from Fiberweb, Simpsonville, SC |
| Adhesive (between first surface layer 62 and elastomeric material layer 64) | hot melt adhesive, BOSTIK H2511, available from Bostik, Middleton, MA, applied at about 10 gsm |
| Elastomeric Material Layer 64 | 62 gsm styrene-butane-styrene film, SOLASTIC, available from Nordenia International AG, Gronau, Germany |
| Adhesive (between elastomeric material layer 64 and second surface layer 63) | hot melt adhesive, BOSTIK H2511, available from Bostik, Middleton, MA, applied at about 10 gsm |
| Second Surface Layer 63 | 31 gsm high elongation carded (HEC), point-bonded nonwoven, FPN 332D available from Fiberweb, Simpsonville, SC |

Many variations in specific materials and construction approaches may be used to achieve the desired stiffness and stretch levels required herein. Other examples of materials and construction approaches are shown in U.S. Published Application Nos. 2007/0143972 and 2007/0157441. Examples of approaches for rendering the extensible zone extensible are described in U.S. Pat. Nos. 4,107,364 and 4,834,741, and in published PCT applications Nos. WO 1992/015446 and WO 1992/015444.

Test Methods

Stiffness Test

Figure 11:
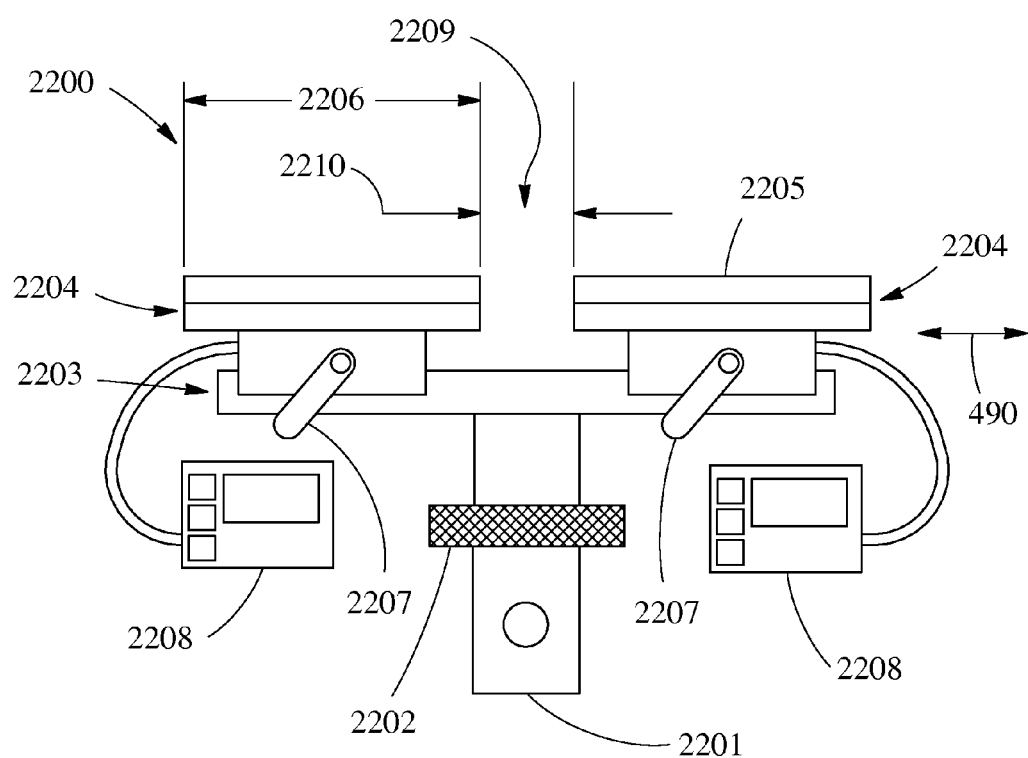
FIG. 11 is an elevation view showing an apparatus for testing the bending stiffness of materials.
Figure 12:
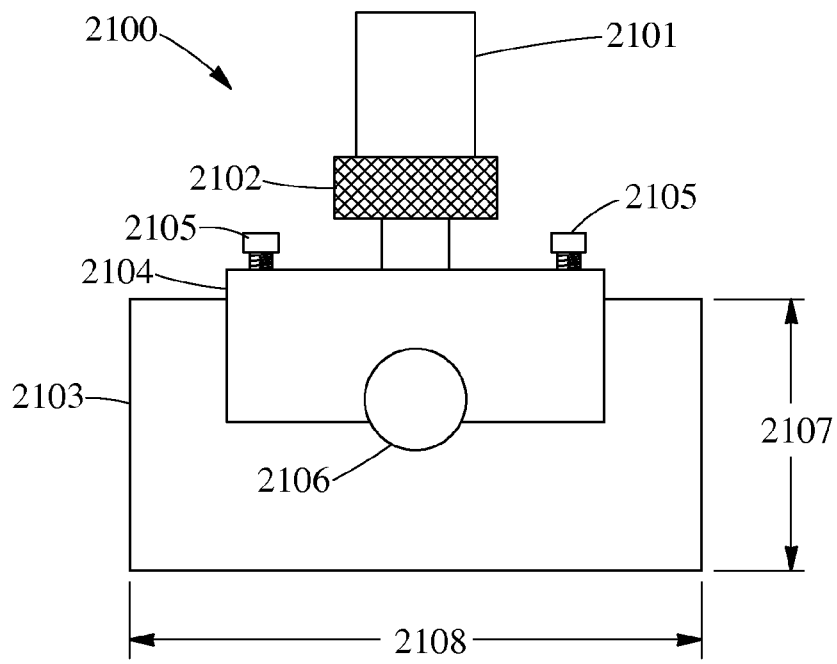
FIG. 12 is a front elevation view showing a plunger for use with the apparatus of FIG. 11.
Figure 13:
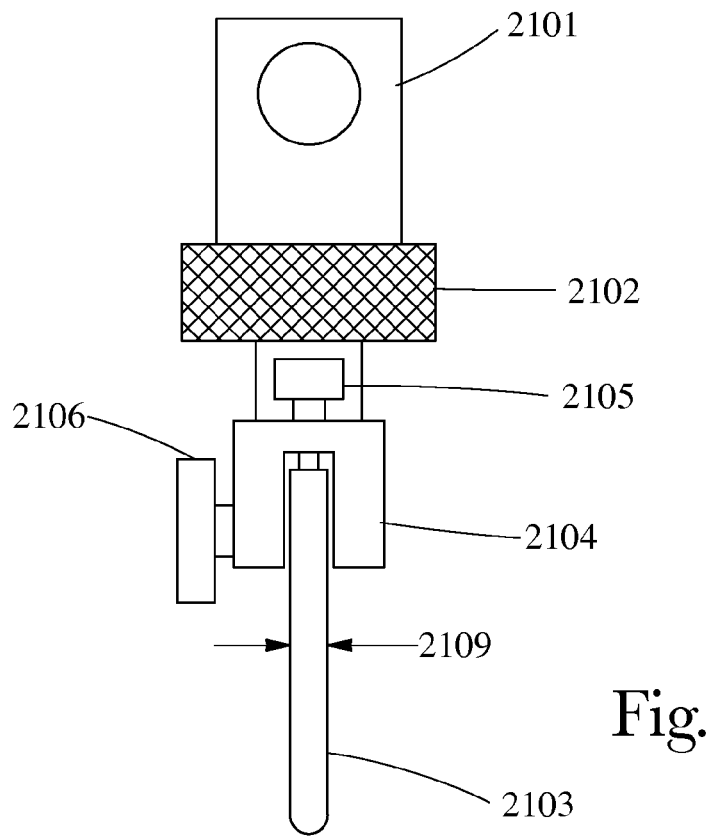
FIG. 13 is a side elevation view showing a plunger for use with the apparatus of FIG. 11.

Stiffness is measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 12 (front view) and FIG. 13 (side view), is used for the upper movable test fixture. Base support platforms 2200, shown in FIG. 11, are used as the lower stationary test fixture. All testing is performed in a conditioned room maintained at about 23 C±2 C and about 50%±2% relative humidity. Herein, width and length of the test specimen are a lateral width and longitudinal length using the directional conventions corresponding to the fastening member from which the specimen is cut, as "lateral width" and "longitudinal length" are defined herein.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 325 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 8.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Precondition specimens at about 23 C±2 C and about 50%±2% relative humidity for 2 hours prior to testing. Die cut a test specimen 13 mm in width by 25.4 mm in length. If the fastening member from which the test specimen is to be cut does not have sufficient material for a 13 mm-wide test specimen, use the full width that is available.

Examine the specimen for any exposed adhesive and deactivate any exposed adhesive by applying baby powder to it as necessary. Place the specimen flat onto the surface of the support platform 2204 over the gap 2209 with the fastener facing upward. If the particular specimen does not contain a fastener (for example, a specimen cut from the intermediate region), orient the specimen such that the fastener side is facing up. Center the specimen across the gap; its length should be parallel to the gap width 2210 and its width should be perpendicular to the gap width 2210. Zero the load cell; start the tensile tester and the data acquisition.

Figure 14:
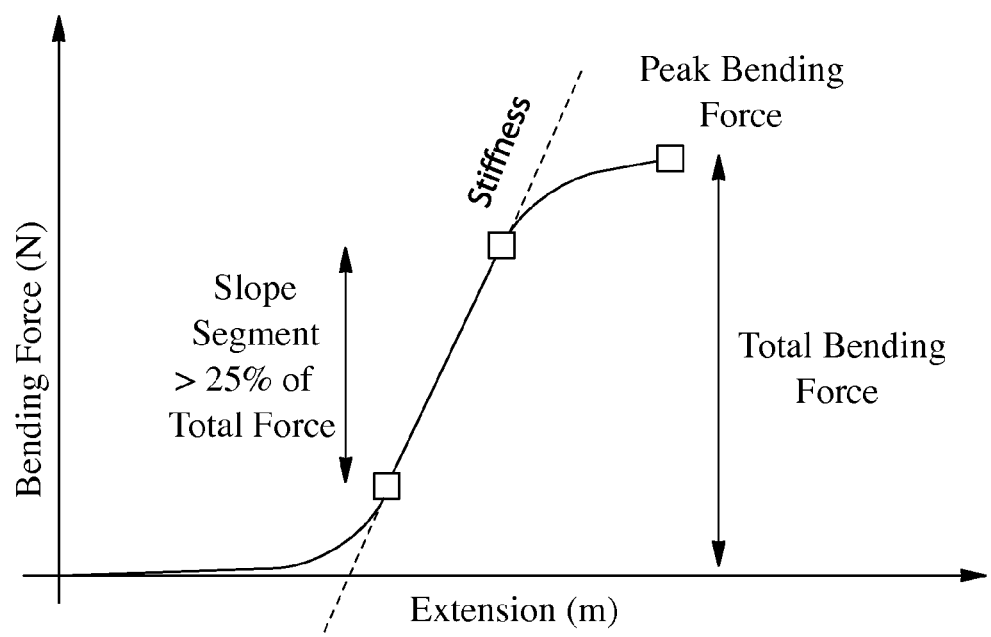
FIG. 14 is a graph showing Peak bending load and slope calculation areas on bending curve.

Program the software to calculate the maximum peak bending force (N) and Stiffness (N/m) from the constructed force (N) verses extension (m) curve. Stiffness is calculated as the slope of the bending force/extension curve for the linear region of the curve (see FIG. 14), using a minimum line segment of at least 25% of the total peak bending force to calculate the slope. If the width of the element is not 13 mm, normalize the actual width to 13 mm as follows:

$$\text{Stiffness}_{(actual\ width)} = [\text{Stiffness}_{(13\ mm)}/13\ mm] \times \text{actual width (mm)}$$

$$\text{peak bending force}_{(actual\ width)} = [\text{peak bending force}_{(13\ mm)}/13\ mm] \times \text{actual width (mm)}$$

Report peak bending force to the nearest 0.1 N and the Stiffness to the Nearest 0.1 N/m.

Extensibility Test

Extensibility of the fastening member is measured using a constant rate of extension tensile tester with computer interface (a suitable instrument is a MTS Alliance under TestWorks 4 software, as available from MTS Systems Corp., Eden Prairie, Minn.) fitted with a suitable load cell. The load cell should be selected to operate with 10% and 90% of its stated maximum load. All testing is performed in a conditioned room maintained at about 23 C±2 C and about 50%±2% relative humidity. Herein, width and length of the specimen are a lateral width and longitudinal length as defined herein. Precondition specimens at about 23 C±2 C and about 50%±2% relative humidity for 2 hours prior to testing.

Prepare fastening member for testing as follows:
1. If the fastening member is attached to an article, cut it free from the article at a location sufficiently inboard of the junction line that a tensile tester's grip can sufficiently grasp the specimen for the testing.
2. Identify the junction line (51 as described in examples herein) and mark a line on the fastening member coincident with the junction line (for example using a fine point pen, such as a fine point Sharpie).
3. Identify the fastening zone inboard extent (88 as described in examples herein) and mark a line on the fastening member coincident with the fastening zone inboard extent (for example using a fine point pen, such as a fine point Sharpie).
4. Lay the fastening member on a substantially flat, horizontal surface and measure width WS as described herein, with no lateral tension force applied to the fastening member.
5. Measure lengths LFP and LEP (as described in examples herein) to the nearest 1 mm, with a steel ruler traceable to NIST.
6. Along fastener zone inboard extent, mark the fastener zone longitudinal midpoint (measure length LFP (as described in examples), the midpoint is at ½ of LFP.

Test the specimen:
1. Insert the outboard end of the fastening member into the upper clamp in the tensile tester such that the clamp is centered in the tensile tester fixture, the clamp width is at least as wide as the length dimension LFP of the fastening member, the face of the clamp (once it grips the specimen) is aligned with the fastener zone inboard extent 88 to within 1 mm, the longitudinal midpoint of the fastener zone inboard extent 88 is aligned with the center of the clamp, and the unclamped portion of the fastening member hangs freely downward from the upper clamp.
2. Insert the inner end of the fastening member into the lower clamp in the tensile tester. The lower clamp width is chosen such that no portion of the fastening member extends beyond the width of the clamp. The face of the clamp (once it grips the specimen) is aligned with the junction line to within 1 mm, and the specimen is oriented such that if a lateral line were drawn from the fastener zone longitudinal midpoint, it would extend vertically and align with the center of the fixture holding the lower clamp.
3. Extend the jaws of the tensile tester such that the distance between the face of the upper clamp and face of the lower clamp is equal to WS. Set gage length equal to WS.
4. Zero the crosshead location and load.
5. Set the tensile tester to extend the specimen at a rate of 254 mm/minute and collect data at a frequency of at least 100 hz.
6. Initiate the test such that the tensile tester's clamp extends the specimen at the defined rate and data is collected into a data file.

Calculate the Results:
1. Determine from the data the overall extensibility under load at 8N, calculated as 100%×[Distance Extended from Zero-point at 8 N load/WS (at no lateral tension load)].

2. Determine from the data the extensibility under load per fastener zone length at 2.1 N/cm-LFP, calculated as 100%×[Distance Extended from Zero-point at 2.1 N/cm-LFP load/WS (at no lateral tension load)], where 2.1 N/cm-LFP load=2.1 N per centimeter length of LFP, for example, if LFP is 3 cm, load of 2.1 N/cm-LFP=6.3 N.

3. Determine from the data the extensibility under load per extensible zone length at 1.0 N/cm-LEP, calculated as 100%×[Distance Extended from Zero-point at 1.0 N/cm-LEP load/WS (at no lateral tension load)], where 1.0 N/cm-LFP load=1.0 N per centimeter length of LEP, for example, if LEP is 6 cm, load of 1.0 N/cm-LFP=6.0 N.

Dimension Methods

Various dimensions and ratios thereof are specified herein. Each dimension is measured according to the following method. All testing is performed in a conditioned room maintained at about 23 C±2 C and about 50%±2% relative humidity. Herein, width and length of the specimen are a lateral width and longitudinal length as defined herein. Precondition specimens at about 23 C±2 C and about 50%±2% relative humidity for 2 hours prior to testing.

Prepare fastening member for testing as follows:
1. Lay the fastener on a substantially flat, horizontal surface.
2. Identify and mark any needed reference lines to enable the measurement (such as the junction line, L0, L25, L75, L100, etc.) (for example using a fine point pen, such as a fine point Sharpie).
3. Measure each needed dimension to the nearest 1 mm using a steel ruler traceable to NIST.
4. Calculate any needed ratios as follows: Ratio=100%× [First Measurement/Second Measurement]. For example, the ratio of the length of L25 relative to L100=100%×[Length of Line L25/Length of Line L100].

Vertical Pull Test

This test is designed to measure the force, displacement as a function of force (and vice versa), and/or work necessary to separate a sample of a hooks fastener component from engagement with a loops component, which components may be used to form a hook-and-loop fastening system, such as often found on wearable articles, including but not limited to many kinds of disposable diapers. In some instances, the loops component may be the same as surrounding outer materials on the article; in some wearable article designs the nature of the outer material alone is sufficient to provide a fibrous surface that is effectively engageable with a hooks component, to provide the desired attachment.

Test Sample Preparation

Figure 15A:
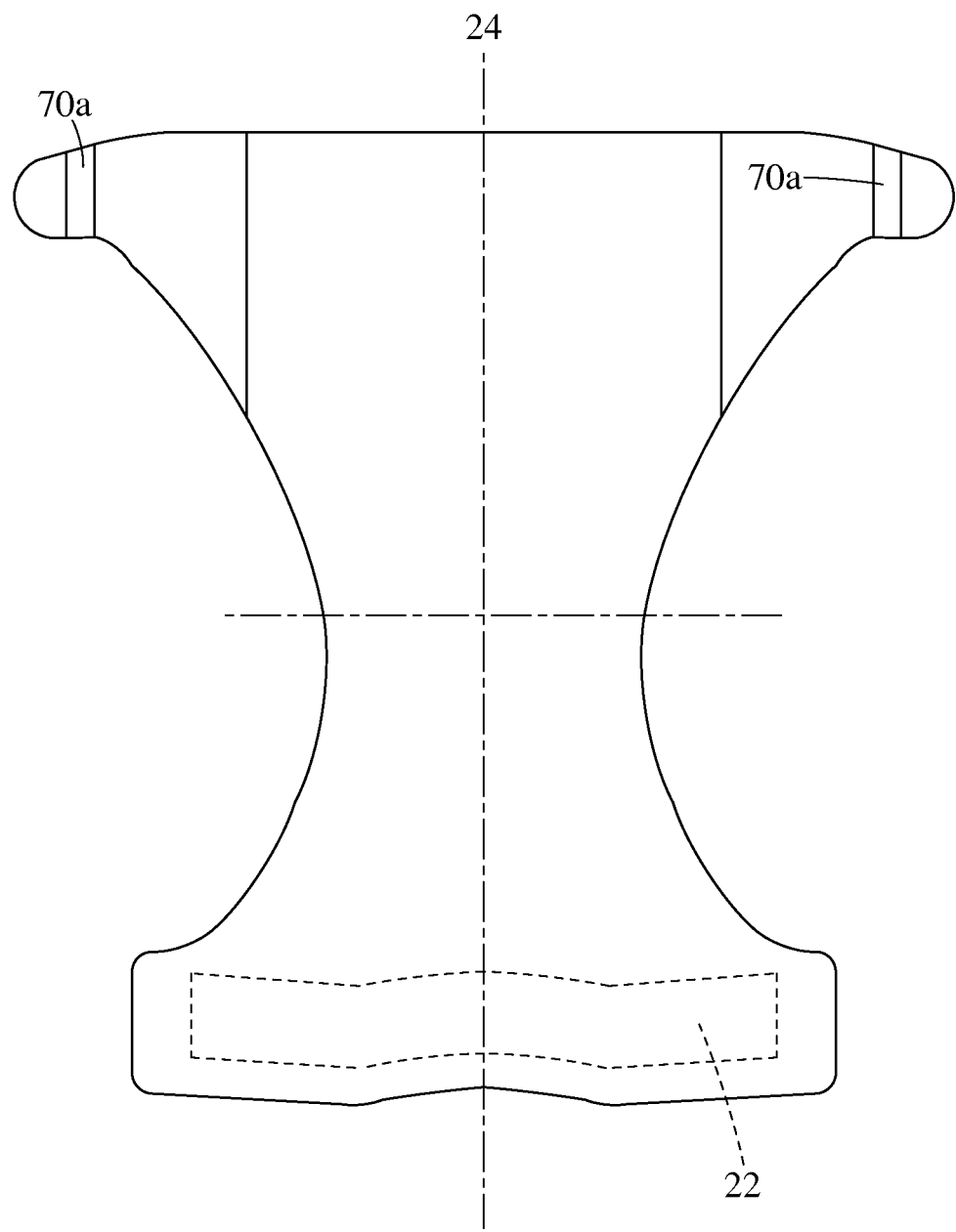
FIG. 15A is a simplified depiction of a wearable article in the form of a diaper, shown extended and laid flat, viewed from above, wearer-facing surface up.
Figure 15B:
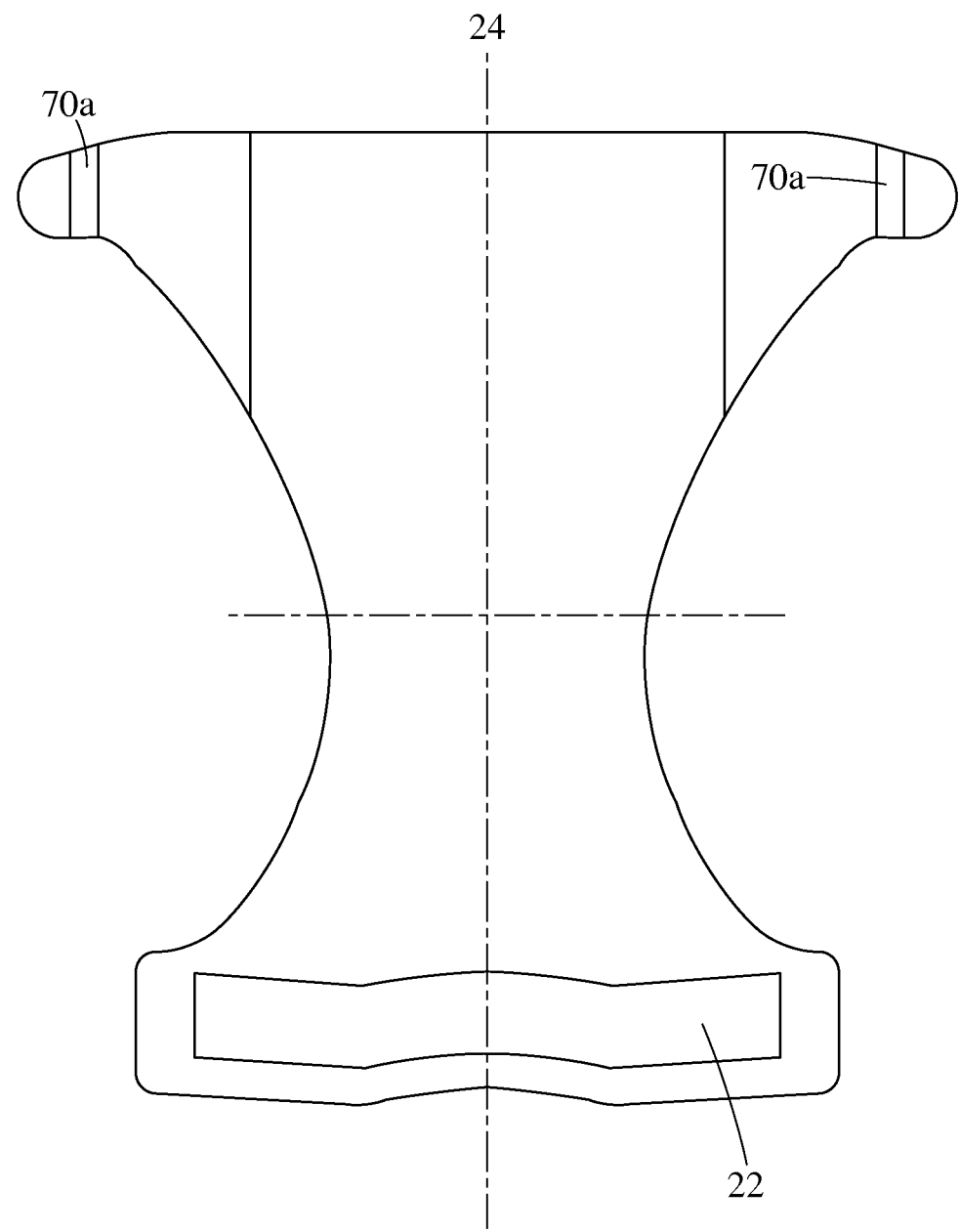
FIG. 15B is a simplified depiction of a wearable article in the form of a diaper, shown extended and laid flat, viewed from above, wearer-facing surface down.
Figure 15C:
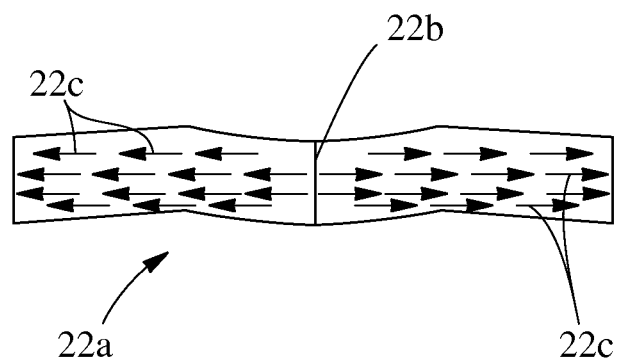
FIG. 15C is a depiction of a sample of landing zone material removed from a wearable article such as depicted in FIGS. 15A and 15B.

Prepare hooks fastener and landing zone material samples for testing as follows:

Landing Zone Material
1. Identify the landing zone portion of the outer surface of the article. (For illustrative example, see FIG. 15B, landing zone 22.)
    a) If the landing zone portion is formed of a layer of material laminated over an underlying layer, remove the landing zone material without damaging it. Use a freeze spray as necessary to weaken bonding by any laminating adhesives, to facilitate separation of the landing zone material ("LZ material") from the underlying layer.
    b) If the layer forming the landing zone cannot be separated from the underlying material without damaging it, or if the landing zone is formed of material that is the same as surrounding material outside the landing zone, cut out a portion of the material of a size sufficient to provide the samples required by the steps below. To the extent possible without damage, remove any waist feature or core material that is beneath the landing zone to reduce bulk created by layers. The remaining material will be the removed landing zone material ("LZ material").
2. Lay the LZ material flat on a table, loops side down. Determine the ordinary direction of pull by the fastening member on the landing zone when the article is in use. Using a permanent felt-tip marker (such as a SHARPIE) and a ruler, draw substantially straight arrows on the LZ material, indicating the ordinary direction of pull on the landing zone, in several locations about the material. (If the wearable article is a diaper, this direction will be perpendicular to and pointing away from the longitudinal axis of the diaper: Using the marker and a ruler, draw a longitudinal (relative the article) line through the center of the LZ material, and draw several arrows on the material substantially perpendicular to the line and pointing away from it, on either side of the line.) (For illustrative example, see FIG. 15C, LZ material 22a, longitudinal line 22b, arrows 22c.)
3. Prepare double-side tape to join the LZ material to the fixture as follows: Join the adhesive side of 3M 1524 Transfer Adhesive to the adhesive side of a strip of 3M 9589 Double Coated Film Tape to form a double-sided tape laminate. (In the event either or both of these products are not available at the time of the test, equivalent product(s) sufficient to adhere the sample to the underlying surface and resist delamination in the test, as described below, may be substituted.)
4. Lay the prepared double-side tape flat on a table, with the 3M 1524 Transfer Adhesive side up. Remove the release backing to expose the adhesive of the 3M 1524 Transfer Adhesive. Gently lay the LZ material, loops side up, onto the exposed adhesive surface of the double-sided tape laminate. Apply substantially even pressure to the LZ material to press it against the adhesive surface, using a pressure of about 25 g/cm$^2$±10% (an appropriate weight having a flat bottom surface may be used). The LZ material should be applied to the tape evenly to avoid forming bubbles or wrinkles. If bubbles or wrinkles having a dimension of greater than about 3 mm in any direction are formed, do not use the portion(s) bearing bubbles or wrinkles in any samples for testing.
5. Cut substantially rectangular samples of the LZ material/ tape laminate at least about 50.8 mm by at least about 22 mm, with the shorter sides substantially parallel with the direction of the arrows. These will be the LZ Samples.

Hook Material
1. Remove the hook patch (illustrative example of hook patch 70a shown in FIG. 15A) from the fastening member without damaging the hook patch. Use a freeze spray as necessary to weaken bonding by any laminating adhesives, to facilitate separation of the hook patch from the underlying layer. If it is not possible to remove the hook patch from the underlying layer without damaging it, then simply cut around its outer edges to sever it from the remaining portions of the fastening member. Lay the separated hook patch on a table, hooks facing down.

2. Prepare double-side tape to join the LZ material to the fixture as follows: Join the adhesive side of 3M 1524 Transfer Adhesive to the adhesive side of a strip of 3M 9589 Double Coated Film Tape to form a double-sided tape laminate. (In the event either or both of these products are not available at the time of the test, equivalent product(s) sufficient to adhere the sample to the underlying surface and resist delamination in the test, as described below, may be substituted.)

3. Lay the prepared double-side tape flat on a table, with the 3M 1524 Transfer Adhesive side up. Remove the release backing to expose the adhesive of the 3M 1524 Transfer Adhesive. Gently lay the hook patch, hooks side up, onto the exposed adhesive surface of the double-sided tape laminate. Apply substantially even pressure to the hook patch to press it against the adhesive surface, using a pressure of about 75 g/cm$^2$±10% (an appropriate weight having a flat bottom surface may be used). The hook patch should be applied to the tape evenly to avoid forming bubbles or wrinkles. If bubbles or wrinkles having a dimension of greater than about 3 mm in any direction are formed, do not use the portion(s) bearing bubbles or wrinkles in any samples for testing.

4. Cut one or more substantially rectangular samples (size of hook patch permitting) from the hook patch/tape laminate 13 mm by 25 mm, ±0.25 mm, with the shorter sides substantially parallel the direction of pull of the hook patch when in ordinary use. These will be the Hook Samples.

Samples of respective landing zone material and hook material that have not been cut from finished manufactured wearable articles, but rather, taken from supplies of such materials prior to manufacture of articles, can be prepared in a manner similar to that set forth above. The materials should be oriented and cut according to the orientation in which they would appear in a finished product, i.e., with shorter sides of the respective rectangular samples parallel with the direction of pull of the hooks against the loops.

Test Equipment

A constant rate of extension tensile tester with computer interface (such as a MTS SYNERGIE 200 tensile tester, controlled with TestWorks 4 software, as available from MTS Systems Corp., Eden Prairie, Minn., or suitable equivalent), fitted with an appropriate load cell is used for this test. The load cell should be selected to be operated within 10% and 90% of its stated maximum load. The tensile tester is set up such that when the crosshead moves downward and compresses samples, a negative force reading is generated to indicate compression.

Figure 16A:
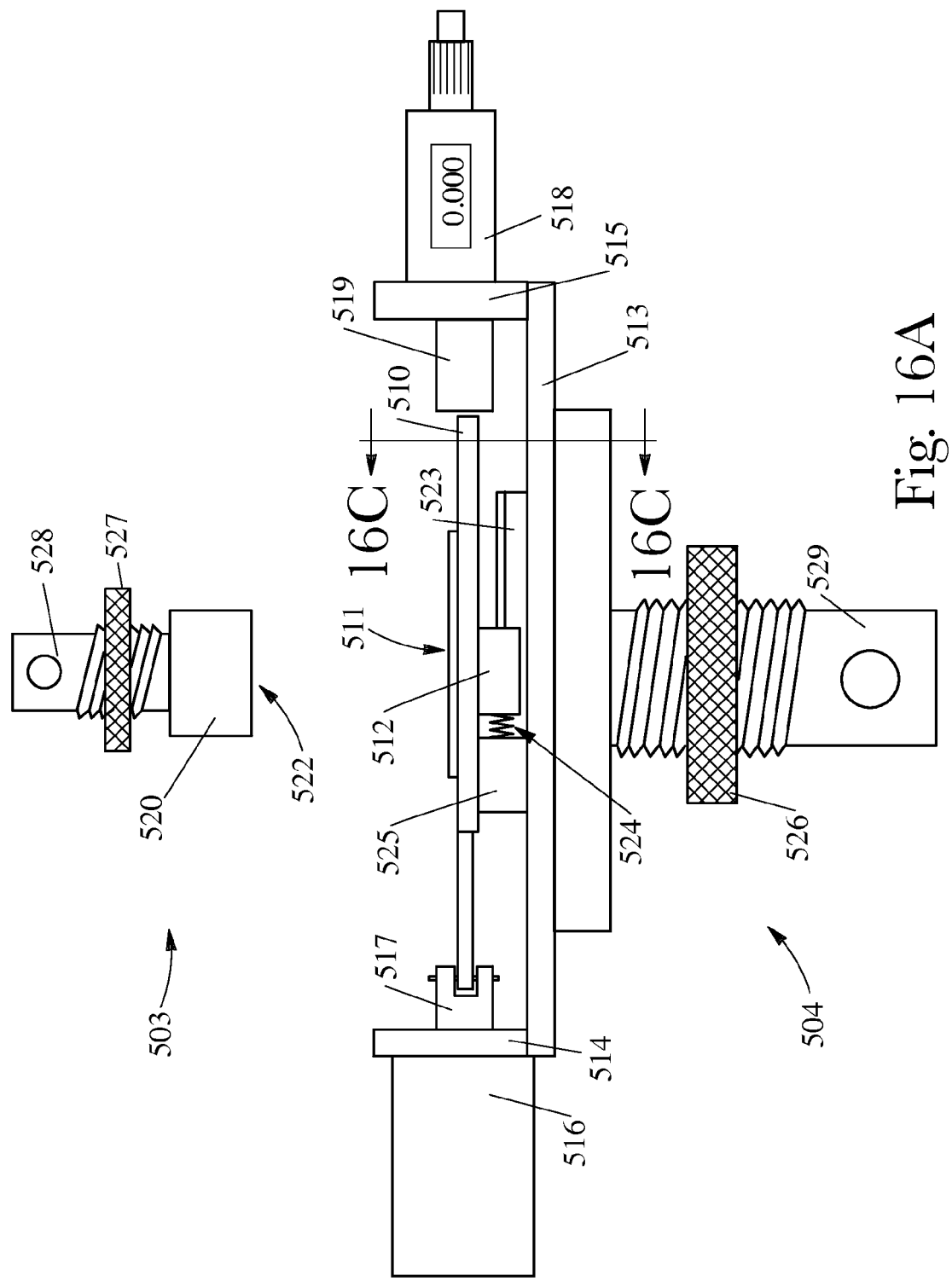
FIG. 16A is a schematic front-view depiction of upper and lower fixtures used in the Vertical Pull Test described herein.

For this test, two custom fixtures must be fabricated. Referring to FIG. 16A, the first fixture 503 includes a rectangular foot 520 that attaches to the load cell of the tester, and has a downward-facing planar surface 522 orthogonal to the path of travel of the crosshead, onto which a Hooks Sample is to be affixed. The second fixture 504 attaches to the bottom, stationary mount of the tensile tester, and consists of a base 513 and a solenoid-activated sliding plate 510 having an upward-facing planar surface 511 orthogonal to the path of travel of the crosshead, onto which the LZ Sample is to be affixed. Thus, when the test is performed, the loops side of the LZ Sample is oriented facing and parallel to, the hooks side of the Hooks Sample.

Still referring to FIG. 16A, the upper fixture 503 consists of a rectangular foot 520 affixed to a suitable mounting device such as an upper mounting shaft 528 adapted to mount to the load cell as affixed to the movable crosshead of the tensile tester. Upper mounting shaft 528 is threaded as shown, and has a locking collar 527. When upper mounting shaft 528 is connected to the mount of the load cell, locking collar 527 is turned against the mount, to immobilize fixture 503 such that the surface 522 remains orthogonal to the travel axis. The foot 520 is formed of aluminum with a downward-facing, planar, brushed-finish surface 522 orthogonal to the path of travel of the crosshead. Downward-facing surface 522 must be of sufficient length and width to accept the entirety of a Hooks Sample, shorter sides extending in a left-right direction, and must be substantially centered about the axis of upper mounting shaft 528.

Figure 16B:
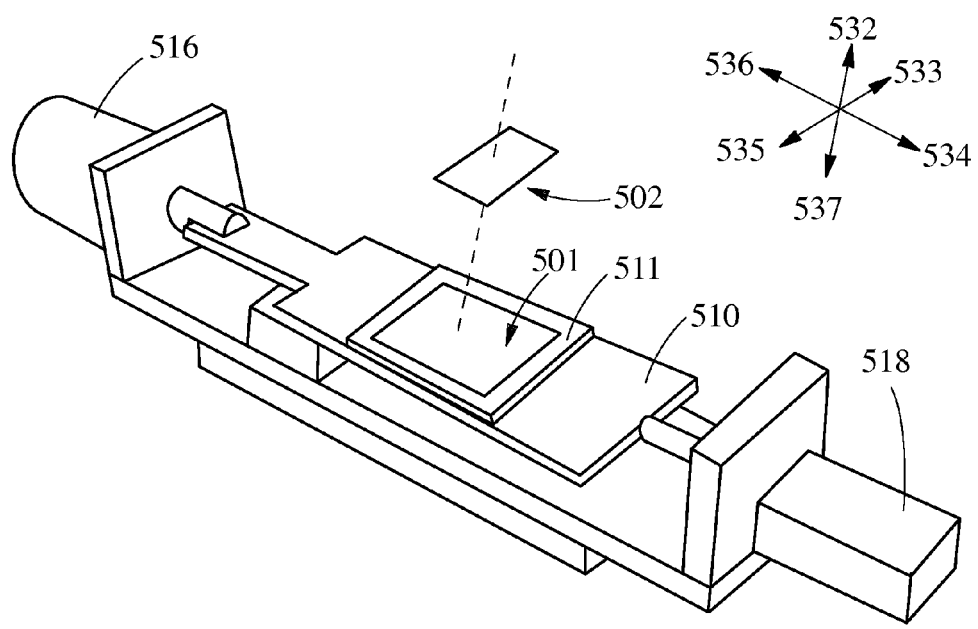
FIG. 16B is schematic perspective-view depiction of the lower fixture used in the Vertical Pull Test described herein, shown with test samples oriented with respect thereto.
Figure 16C:
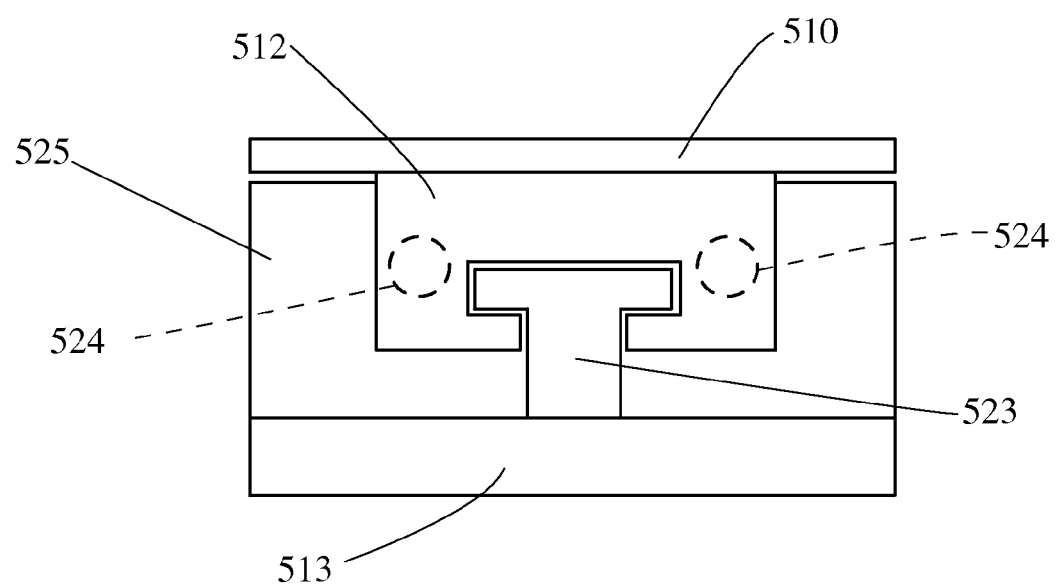
FIG. 16C is a view of cross-section C-C taken through the schematic depiction of the lower fixture shown in FIG. 16A.

Referring to FIGS. 16A-16C, the lower fixture 504 consists of a base 513, having two vertical plates 514 and 515 affixed at each end. An electronic solenoid 516 (Sealed Linear Solenoid Actuator Extended Life—Sealed Pull type, Part No. 9719K112, McMaster Carr, Atlanta, Ga.—or suitable equivalent) is mounted on the left vertical plate 514, with its plunger 517 extending to the right and protruding through a hole in plate 514; the hole is large enough to permit free left-right movement of plunger 517. A micrometer 518 (Micrometer Head, Electronic type, 1" Max measuring range 0.00005" resolution, Part No. 74477589, MSC Industrial Supply, Melville N.Y.—or suitable equivalent) is mounted on the right vertical plate 515, with its spindle 519 extending to the left and protruding through a hole in plate 515; the hole is large enough to permit free left-right movement of the spindle 519. The solenoid plunger 517 and the micrometer spindle 519 are substantially coaxial. The base 513 is affixed to a suitable mounting device that includes lower mounting shaft 529, adapted to mount to the stationary mount of the tester. Lower mounting shaft 529 is threaded as shown, and has a locking collar 526. When lower mounting shaft 529 is mounted to the stationary mount of the tester, locking collar 526 is turned against the stationary mount to immobilize the base 513 relative the stationary mount of the tester, such that it will remain stationary with the stationary mount, so as to maintain surface 511 orthogonal to the path of travel of the crosshead during testing.

A horizontally sliding plate 510 has an integral tab as shown, connected to the solenoid plunger 517. Sliding plate 510 is affixed to plate guide 512, which has a horizontal, left-right track machined therein which mates with guide rail 523 to allow free left-right movement, with no significant vertical play. (Mating plate guide 512 and guide rail 523 are acquired from McMaster-Carr, Atlanta, Ga., Part No. 9880K3 (Frelon Plain-Bearing Guide Block); and Part No. 9880K13 (Frelon Plain-Bearing Rail).)

Guide rail 523 is affixed to base 513. As a consequence of this configuration, plate guide 512, and correspondingly, sliding plate 510, may move in a horizontal, left-right direction relative base 513, in response to activation of solenoid 516. Rightward movement of sliding plate 510 is limited by the distal end of micrometer spindle 519, which sliding plate 510 abuts in the rightwardmost position. Leftward movement of sliding plate 510 is limited by standoff 525, which plate guide 512 abuts in the leftwardmost position.

Guide rail 523 terminates at standoff 525, which also is affixed to base 513. Standoff 525 holds two recessed springs 524 that apply a sufficient force against the plate guide 512 to push the sample plate 510 to abutting relationship with the distal end of micrometer spindle 519 when solenoid 516 is not activated. Once activated, solenoid 516 pulls the sliding plate 510 toward the left, until plate guide 512 stops against standoff 525.

An aluminum sample plate having a planar, brushed-finish upward-facing surface 511 is affixed to the top surface of the sliding plate 510. Upward-facing surface 511 must be of sufficient length and width to accept the entirety of an LZ Sample, shorter side extending in a left-right direction, and must be substantially centered about the axis of lower mounting shaft 529.

The fixtures are configured such that when both upper fixture 503 and lower fixture 504 are installed on the tester, upper mounting shaft 528 and lower mounting shaft 529 are substantially coaxial, i.e., are aligned along the direction of pull of the crosshead. The fixtures are configured such that when Hooks and LZ Samples are properly placed thereon and the fixtures are installed on the tester, the geometric centers of the rectangular shapes of the Samples are substantially aligned on a vertical axis when the Samples are engaged, prior to being offset by a Shear Displacement. The fixtures should be adapted such that, when installed on the tester, downward surface 522 on upper fixture 503 and upward surface 511 on lower fixture 504 are parallel to each other and orthogonal to the vertical line of travel of the crosshead.

Test Protocol

All testing is performed in a conditioned room maintained at about 23° C.±2 C.° and about 50%±2% relative humidity. Precondition the samples at about 23° C.±2 C.° and about 50%±2% relative humidity for 2 hours prior to testing.

The rectangular Hooks Sample 502 and LZ Sample 501 are to be affixed onto the downward surface 522 and upward surface 511, respectively, with short sides along the left-right direction (in FIG. 16B, along direction 534-536), and in a relative rotational orientation within a horizontal plane corresponding with the direction of shearing force the materials would encounter in use on a finished article, relative the Shear Displacement effected by solenoid 516. Referring to FIGS. 16A and 16B, solenoid 516 will move the LZ Sample 501 to the left (direction 536 indicated in FIG. 16B) relative the Hooks Sample 502, for the selected Shear Displacement. In view of this, for the Hooks Sample 502 and LZ Sample 501 to be properly oriented relative each other on the fixtures, they should be placed thereon such that when engaged during the test in facing relationship they represent the manner in which the corresponding materials would be (a) oriented; and (b) urged by shearing force, relative each other when engaged on an article. In like fashion, any raw material samples are tested as they would be oriented on a finished article.

Remove the release backing on an LZ Sample. Gently place the LZ Sample on upward-facing surface 511, oriented as described above. After proper alignment, the LZ Sample should be affixed to surface 511 using a force of approximately 250 g, applied uniformly across the entire surface area of the sample, while surface 511 is oriented horizontally. Next, remove the release backing on a Hooks Sample. Gently place the Hooks Sample on downward-facing surface 522, oriented as described above. After proper alignment, the Hooks Sample should be affixed to surface 522 using a force of approximately 250 g, applied uniformly across the entire surface area of the sample, while surface 522 is oriented horizontally, facing up.

Install the lower fixture 504 and upper fixture 503 onto the tensile tester. Set the gage length between surfaces 522 and 511 to 50 mm. Zero the load cell.

Activate the solenoid 516 to move the sliding plate 510 so that the plate guide 512 abuts the standoff 525. Adjust the micrometer 518 to extend the spindle 519 until it abuts the sliding plate 510. Zero the micrometer. Then, adjust the micrometer to retract the spindle 519 to the desired Shear Displacement (i.e., 1.00 mm or 2.00 mm, ±0.005 mm). Deactivate the solenoid 516 to allow the sliding plate 510 to move to the right so that it abuts the distal end of the micrometer spindle 519. (To assure calibration, the micrometer should be reset to the desired shear distance after every 20 samples.)

The tensile tester is programmed to move the crosshead down at 5.0 mm/sec until it moves 40 mm, and then further descend at a rate of 0.5 mm/sec, until 1.00 N of compressive force is applied to the Samples to engage them. After 3 seconds, the solenoid 516 is activated to move the sliding plate 510 to the left (Shear Displacement) position, and held for an additional 3 seconds. Next, set the crosshead to zero.

Start the tensile tester program to effect movement of the crosshead up 50 mm at 5 mm/sec and collect data. Plot the data as force (N) versus vertical crosshead displacement (mm).

Each LZ Sample and each Hooks Sample may be used for only one test. During the test, confirm that neither of the samples partially delaminates from the surfaces 511, 522. If any delamination is detected, the result is invalid.

Following removal of a sample from a surface, clean the surface of any adhesive residue using appropriate solvent, and allow the surface to dry before affixing a new sample.

The following calculations are performed from the force/displacement curve:

1. Adjusted Crosshead Displacement ("ACD"): The positive displacement (mm) at which the force exceeds 0.0 N. If as a result of shearing the sample, the starting force exceeds 0.0 N, the adjusted crosshead displacement is taken as 0.00 mm. Reported to ±0.01 mm.
2. Vertical Peak Load: The maximum force (N) sustained by the sample pair, recorded between the ACD and 50 mm Displacement. Reported to ±0.01 N.
3. Displacement at Vertical Peak Load: The displacement (mm) from the ACD to the Vertical Peak Load. Reported to ±0.01 mm.
4. Greatest Vertical Load between 0.0 and 0.5 mm Displacement: The maximum force (N) sustained by the sample pair, recorded between the ACD and ACD+0.5 mm Displacement. Reported to ±0.1 N.
5. Greatest Vertical Load between 0.0 and 1.0 mm Displacement: The maximum force (N) sustained by the sample pair, recorded between ACD and ACD+1.0 mm Displacement. Reported to ±0.1 N.
6. Energy for Complete Removal: Energy (mJ), i.e., total area under the force/displacement curve, between ACD and 50 mm displacement. Report to ±0.1 mJ.
7. Energy to Resist Removal: Energy (mJ), i.e., total area under the force/displacement curve, between ACD and Displacement to Peak. Report to ±0.1 mJ.

For obtaining results for a selected landing zone and hooks combination for purposes herein, test a minimum of ten landing zone/hooks sample pairs (n=10) and report as an average.

The Vertical Pull Test may be used to compare the performance of any particular combination of loops material and hooks material with any other particular such fastening combination, and may be useful in determining which combination is more suitable for use in a particular application. Accordingly, the Vertical Pull Test may be used to select a fastening combination of landing zone material and hooks material suitable for use on a wearable article, such as, but not limited to, a disposable diaper.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper, comprising:
    a chassis having a front waist region, a rear waist region, a landing zone disposed on the front waist region, the landing zone comprising a loop material, and
    an integrally-formed, highly extensible fastening member extending laterally from the rear waist region to an outboard end and having a fastening member length (L), an extensible zone bounded by inboard and outboard extensible zone extents, a strengthened end region disposed outboard of the extensible zone, a fastener zone disposed on said strengthened end region, said fastener zone having first and second inboard fastener zone corners, said fastener zone having a Stiffness of at least about 1,500 N/m and having a fastener disposed thereon, the strengthened end region having an inboard length (LR) that is less than the fastening member length (L), the fastener comprising a hook material, wherein the loop material and the hook material form a fastening combination,
    wherein said fastening member extends from a junction line along a stretch direction transverse to said junction line, and ends at the outboard end, wherein said junction line connects first and second longitudinally outermost junction points on a first longitudinally outermost lateral edge and an opposing second longitudinally outermost lateral edge, respectively, of said fastening member, said first longitudinally outermost lateral edge having a first profile beginning at said first longitudinally outermost junction point and ending at said outboard end, and said second longitudinally outermost lateral edge having a second profile beginning at said second longitudinally outermost junction point and ending at said outboard end;
    wherein said fastening member has an acting width (WA) measured from an outboard edge of said fastener zone to said inboard extensible zone extent; said acting width is bounded by longitudinal lines W0 and W100, and said acting width may be divided into four equal portions by longitudinal lines W25 at 25% of said acting width, W50 at 50% of said acting width, and W75 at 75% of said acting width; said fastening member has lengths L0, L25, L50 and L100 measurable along lines W0, W25, W50, and W100, respectively, and the following relationships exist:
        at least one of said first and second profiles has an inflection point approximately between lines W25 and W50, at which said at least one of said first and second profiles changes curvature from concave to convex;
        L0 is at least about 25% of L100;
        L25 is at least about 30% of L100; and
        L50 is at least about 50% of L100.

2. The disposable diaper of claim 1 wherein said first profile intersects a first line segment connecting said first longitudinally outermost junction point and said first inboard fastener zone corner, at a first intersection point inboard of said first inboard fastener zone corner.

3. The disposable diaper of claim 1 wherein said inboard length (LR) of said strengthened end region is within the range of about 66% to about 80% of said fastening member length (L).

4. The disposable diaper of claim 1, wherein, at a 1 mm Shear Displacement, the fastening combination sustains a Vertical Peak Load of at least 4.0 N.

5. The disposable diaper of claim 4 wherein, at a 1 mm Shear Displacement, the fastening combination sustains a Greatest Vertical Load between 0.0 and 0.5 mm Displacement of at least 1.5 N.

6. The disposable diaper of claim 4 wherein, at a 1 mm Shear Displacement, the fastening combination sustains a Greatest Vertical Load between 0.0 and 1.0 mm Displacement of at least 3.0 N.

7. The disposable diaper of claim 4 wherein, at a 1 mm Shear Displacement, the fastening combination sustains a Greatest Vertical Load between 0.0 and 0.5 mm Displacement of at least 1.5 N; and undergoes a Displacement at Vertical Peak Load of at least about 0.5 mm.

8. The disposable diaper of claim 4 wherein, at a 1 mm Shear Displacement, the fastening combination sustains a Greatest Vertical Load between 0.0 and 1.0 mm Displacement of at least 3.0 N; and undergoes a Displacement at Vertical Peak Load of at least about 0.5 mm.

9. The disposable diaper of claim 4, wherein, at a 2 mm Shear Displacement, the fastening combination sustains a Vertical Peak Load of equal to or greater than 4.0 N.

10. A disposable diaper, comprising:
    a chassis having a front waist region, a rear waist region, a landing zone disposed on the front waist region, the landing zone comprising a loop material, and
    an extensible fastening member extending laterally from the rear waist region to an outboard end and having a fastening member length (L), an extensible zone bounded by inboard and outboard extensible zone extents, a strengthened end region disposed outboard of the extensible zone, a fastener zone disposed on said strengthened end region, said fastener zone having first and second inboard fastener zone corners, said fastener zone having a Stiffness of at least about 1,500 N/m and having a fastener disposed thereon, the strengthened end region having an inboard length (LR) that is less than the fastening member length (L), the fastener comprising a hook material, wherein the loop material and the hook material form a fastening combination,
    wherein said fastening member extends from a junction line along a stretch direction transverse to said junction line, and ends at the outboard end, wherein said junction line connects first and second longitudinally outermost junction points on a first longitudinally outermost lateral edge and an opposing second longitudinally outermost lateral edge, respectively, of said fastening member, said first longitudinally outermost lateral edge having a first profile beginning at said first longitudinally outermost junction point and ending at said outboard end, and said second longitudinally outermost lateral edge having a second profile beginning at said second longitudinally outermost junction point and ending at said outboard end;

wherein said fastening member has an acting width (WA) measured from an outboard edge of said fastener zone to said inboard extensible zone extent; said acting width is bounded by longitudinal lines W0 and W100, and said acting width may be divided into four equal portions by longitudinal lines W25 at 25% of said acting width, W50 at 50% of said acting width, and W75 at 75% of said acting width; said fastening member has lengths L0, L25, L50 and L100 measurable along lines W0, W25, W50, and W100, respectively, and the following relationships exist:

at least one of said first and second profiles has an inflection point approximately between lines W25 and W50, at which said at least one of said first and second profiles changes curvature from concave to convex;

L0 is at least about 25% of L100;

L25 is at least about 30% of L100; and

L50 is at least about 50% of L100.

11. The disposable diaper of claim 10 wherein said fastening member is integrally-formed and highly extensible and said first profile intersects a first line segment connecting said first longitudinally outermost junction point and said first inboard fastener zone corner, at a first intersection point inboard of said first inboard fastener zone corner.

12. The disposable diaper of claim 10 wherein said inboard length (LR) of said strengthened end region is within the range of about 66% to about 80% of said fastening member length (L).

13. The disposable diaper of claim 10, wherein, at a 1 mm Shear Displacement, the fastening combination sustains a Greatest Vertical Load between 0.0 and 0.5 mm Displacement of at least about 1.5 N.

14. The disposable diaper of claim 13 wherein, at a 1 mm Shear Displacement, the fastening combination undergoes a Displacement at Vertical Peak Load of at least about 0.5 mm.

15. The disposable diaper of claim 13, wherein, at a 2 mm Shear Displacement, the fastening combination sustains a Vertical Peak Load of equal to or greater than 1.5 N.

* * * * *